United States Patent
Rieunier et al.

(10) Patent No.: US 9,481,720 B2
(45) Date of Patent: Nov. 1, 2016

(54) BNP(1-32) EPITOPE AND ANTIBODIES DIRECTED AGAINST SAID EPITOPE

(75) Inventors: Francois Rieunier, Bois d'Arcy (FR); Isabelle Giuliani, Garches (FR); Sylvie Villard-Saussine, Issy les Moulineaux (FR)

(73) Assignee: BIO-RAD INNOVATIONS, Marnes la Coquette (FR)

( * ) Notice: Subject to any disclaimer, the term of this patent is extended or adjusted under 35 U.S.C. 154(b) by 892 days.

(21) Appl. No.: 12/733,005

(22) PCT Filed: Aug. 1, 2008

(86) PCT No.: PCT/EP2008/060188
§ 371 (c)(1),
(2), (4) Date: Mar. 26, 2010

(87) PCT Pub. No.: WO2009/019236
PCT Pub. Date: Feb. 12, 2009

(65) Prior Publication Data
US 2010/0209939 A1    Aug. 19, 2010

(30) Foreign Application Priority Data
Aug. 3, 2007   (FR) ...................... 07 05711

(51) Int. Cl.
*C07K 14/58*    (2006.01)
*G01N 33/74*    (2006.01)

(52) U.S. Cl.
CPC ............... *C07K 14/58* (2013.01); *G01N 33/74* (2013.01); *G01N 2333/58* (2013.01); *G01N 2800/32* (2013.01)

(58) Field of Classification Search
CPC .. C07K 14/58; C07K 16/26; C07K 2317/34; C07K 2317/50; C07K 2317/565; G01N 33/531; G01N 33/543; G01N 33/74; G01N 2333/58; G01N 2800/32
USPC ........... 435/7.1, 7.92, 7.93, 7.94, 69.3, 69.4, 435/70.21, 331, 336, 967, 975; 436/518, 436/547, 548, 8, 15, 811, 817; 530/324, 530/325, 326, 327, 328, 387.9, 388.24, 530/389.2, 391.1, 391.3, 806
See application file for complete search history.

(56) References Cited

U.S. PATENT DOCUMENTS

| 6,114,180 | A  | * | 9/2000  | Doth et al. ..................... 436/531 |
| 6,162,902 | A  | * | 12/2000 | Mischak et al. ......... 530/388.24 |
| 7,056,658 | B2 |   | 6/2006  | Valenzuela et al. ............. 435/5 |
| 7,553,937 | B2 | * | 6/2009  | Pau et al. .................. 530/387.9 |
| 7,731,965 | B2 | * | 6/2010  | Shih et al. ................. 424/141.1 |
| 7,998,480 | B2 | * | 8/2011  | Brophy et al. ............. 424/133.1 |
| 8,013,112 | B2 | * | 9/2011  | Wu et al. ...................... 530/300 |
| 2005/0148024 | A1 | * | 7/2005 | Buechler ........................ 435/7.1 |
| 2005/0215482 | A1 | * | 9/2005 | Blaschuk ............. C07K 14/705 514/4.8 |

FOREIGN PATENT DOCUMENTS

| EP | 2135087 | 12/2009 |
| WO | 2004014952 | 2/2004 |
| WO | WO 2006/088700 | 8/2006 |
| WO | 2007/010256 | * 1/2007 |

OTHER PUBLICATIONS

Harlow et al., 1988. Antibodies. A Laboratory Manual, Cold Spring Harbor Laboratory, Cold Spring Harbor. pp. 72-77.*
Hytest Technotes, Aug. 2010. Human ProBNP and proBNP-derived peptides (BNP and NT-proBNP). Downloaded from www.hytest.fi/resources/technotes/ on May 7, 2015.*
Seferian et al. "The Brain Natriuretic Peptide (BNP) Precursor is the Major Immunoreactive Form of BNP in Patients with Heart Failure." Clinical Chemistry, vol. 53, No. 5, May 2007, pp. 866-873.
HyTest Markers of Cardiovascular Diseases Catalog—Oct. 2005.
HyTest Markers of Cardiovascular Diseases Catalog—Jun. 2007.
HyTest Tech Notes—Jun. 2007.
Tamm et al. Novel Immunoassay for quantification of brain natriuretic peptide and its precursor in human blood. Clinical Chemistry 54:9, 1511-1518 (2008).
Hytest Markers of Cardiovascular Diseases Catalog—Nov. 2008.
Hytest General Catalog—2009-2010.
Hytest General Catalog—2010-2011.
Hytest's supplementary experimental data to MAb 24C5 (2015).
Grewal et al. B-type natriuretic peptide: A new marker for congestive heart failure. BCMJ 46:24-29, vol. 46, No., Jan., Feb. 2004.
Tsutamoto et al. Relationship between renal function and plasma brain natriuretic peptide in patients with heart failure. Journal of the American College of Cardiology, vol. 47, No. 3, 2006.
Nakagawa et al. Plasma concentrations of brain natiuretic peptide in patients with acute ischemic stroke. Cerebrovascular Disease 19:157-164, Jan. 11, 2005.
Dao et al. Utility of B-Type natriuretic peptide in the diagnosis of congestive heart failure in an urgent-care setting. Journal of American College of Cardiology, vol. 37, No. 2, 2001, 379-385.
Chan et al. Brain Natriuretic peptide as a potential marker of diastolic dysfunction in Type 2 diabetes. Diabetes Care 24:2019 (2001).
Kohler et al. Pillars Article: Continuous cultures of fused cells secreting antibody of predefined specificity. Nature, 1975, 256 (5517):495-497.
Lerner. How to make a hybridoma. The Yale Journal of Biology and Medicine 54(1981), 387-402.
Partidos et al. The effects of a flanking sequence on the immune response to a B and a T cell epitope from the fusion protein and measles virus. Journal of General Virology (1992), 73, 1987-1994.

(Continued)

Primary Examiner — Jacob Cheu
(74) Attorney, Agent, or Firm — Jacobson Holman PLLC

(57) ABSTRACT

The present invention relates to a polypeptide carrying a human BNP(1-32) epitope according to Formula (I): $a_1$-$R_1$-$X_1$-FGRKMDR-$X_2$-$R_2$-$a_2$ as well as ligands specific of the FGRKMDR epitope.

8 Claims, 11 Drawing Sheets

(56) References Cited

OTHER PUBLICATIONS

Grewal et al. Hindrance of binding to class II major histocompatibility complex molecules by a single amino acid residue contiguous to a determinant leads to crypticity of the determinant as well as lack of response to the protein antigen. Proc Natl Acad, vol. 92, pp. 1779-1783. Feb. 1995.
Hudson et al. Engineered antibodies, (2003) Nature Medicine 9:129-134.
Hollinger et al. Engineered antibody fragments and the rise of single domains. Nature Biotechnology 23:1126-1136. (2005).
Maisel. B-type natriuretic peptide levels: diagnostic and prognostic in congestive heart failure. Circulation 105:2328-2331. (2002).
Doust et al. The role of BNP testing in Heart Failure (2006) Ameri Fam Physic 74:1893-1898.
Technical Information. N-Terminal Acetylation and C-Terminal Amidation of Peptides (2004) Thermo Electron Corp.
Guiliani et al. Assay for Measurement of Intact B-type Natriuretic Peptide Prohormone in Blood (2006) Clinical Chemistry 52:6, 1054-1061.

* cited by examiner

| SEQ ID NO: | 13 | 14 | 15 | 16 | 17 |

Linear correlation between BNP(1-32) and proBNP(1-108) in congestive heart failure according to NYHA class Linear correlation between BNP(1-32) and proBNP(1-108) in acute coronary syndrome Detection of glycosylated and non-glycosylated proBNP(1-108)

BNP(1-32) EPITOPE AND ANTIBODIES DIRECTED AGAINST SAID EPITOPE

This is a national stage of PCT/EP08/060188 filed Aug. 1, 2008 and published in English, which has a priority of French no. 07 05711 filed Aug. 3, 2007, hereby incorporated by reference.

The invention relates to human brain natriuretic peptides (BNP) and in vitro diagnosis of congestive heart failure in humans. More particularly, the invention relates to a new epitope present in the BNP(1-32) molecule, the antibodies directed against said epitope, in particular the 20G7 monoclonal antibody, a method for the immunological assay of BNP(1-32) and proBNP(1-108) and respective fragments thereof using such an antibody, and testing kits for carrying out said assays.

Congestive heart failure is a common clinical syndrome, in particular among the elderly. It normally manifests itself in the form of an insidious triggering of non-specific symptoms, such as coughing upon physical exertion, fatigue and the appearance of peripheral oedema. The diagnosis and assessment of the severity of the affection (graded in stages I to IV NHYA in accordance with the New York Heart Association) are based on the combined interpretation of clinical signs and results of specific tests and examinations (echocardiography, scintigraphy, exercise test, etc.).

Due to the severity of congestive heart failure and also the high patient care costs, early diagnosis of this syndrome is obviously highly desirable as this would contribute to the implementation of treatments suitable for avoiding or delaying rapid progression of the syndrome to severe congestive heart failure. It is therefore necessary to identify those people at risk of congestive heart failure and/or unfavourable prognosis or subsequent complications. This would also make it possible to propose the same tools for (quickly, simply and cost-effectively) therapeutically monitoring patients undergoing treatment. Nowadays, such methods for the diagnosis, prognosis and monitoring of congestive heart failure are in place and are described below, but they have proved to be somewhat unsatisfactory and are not completely informative.

Acute coronary syndromes (ACS) are also a current major health problem. They comprise the following heart diseases: Q-wave myocardial infarction, myocardial infarction with or without ST-segment elevation, threat of myocardial infarction or unstable angina.

The diagnosis, prognosis and monitoring of ACSs are also of the utmost importance in the medical community. The assay of natriuretic peptides (BNP(1-32), NT-proBNP(1-76), and proBNP(1-108)) is of high interest in these applications.

The same also applies to cases of dyspnoea (a disease characterised by breathing difficulties), cerebrovascular accidents (CVA) (also known as "stroke" or "apoplexy"), and associated pathologies such as kidney failure and diabetis associated with these pathologies.

Presymptomatic markers which may predict congestive heart failure have long been sought after. In this respect, it has been shown that cardiomyocytes produce and secrete peptides with natriuretic activity: a peptide of auricular origin, ANP (Atrial Natriuretic Peptide) discovered in rats by de Bold et al. Life Science 1981, vol. 28(1): 89-94, and a natriuretic peptide of auriculo-ventricular origin known as BNP (Brain Natriuretic Peptide) discovered by the inventors of patent EP 418 308 and by Sudoh et al. (1988) *Nature* 332: 78-81 in pigs and in humans.

The precursor of BNP, preproBNP(1-134), is the form of storage of the molecule inside cardiomyocytes. Said precursor is cleaved during and/or after secretion thereof in order to release a signal peptide and proBNP(1-108). ProBNP(1-108) consists in a polypeptide of 108 amino acids of the sequence:
$H_1$PLGSPGSASDLETSGLQEQRNHLQGKLSELQVEQT SLEPLQESPRPTGVWKSREVATEG IRGHRKMVLYTLRAPR$_{76}$S$_{77}$PKMVQGSGCFGRKMDR ISSSSGLGCKVLRRH$_{108}$ (SEQ ID NO: 1).

It is cleaved before and/or during secretion thereof, between the Arg$_{76}$ and Ser$_{77}$ amino acids into, on the one hand, BNP, also known as BNP(77-108) or BNP-32, or even BNP(1-32) (the term which will be used hereinafter), and the N-terminal part of the prohormone, BNP(1-76), also known as the N-terminal fragment of proBNP or NT-proBNP(1-76) (term which will be used hereinafter).

BNP(1-32), the vasoactive form of the molecule, consists in a peptide of 32 amino acids of the sequence: $S_1$PKMVQGSGCFGRKMDRISSSSGLGCKVLRRH$_{32}$ (SEQ ID NO: 2)

17 amino acids form a loop closed by a disulphide bond between the two oxidised cysteine residues ($C_{10}$ and $C_{26}$), said loop being surrounded upstream by 9 amino acids (which constitute the N-terminal part), and downstream by 6 amino acids (which constitute the C-terminal part).

The integrity of the loop is important for obtaining good biological activity. Of the 17 residues forming the loop, 11 are also conserved in the 2 other natriuretic peptides, which are ANP (A-type natriuretic peptide) and CNP (C-type natriuretic peptide).

NT-proBNP(1-76) is formed by the 76 N-terminal amino acids of proBNP(1-108) and has the following sequence: $H_1$PLGSPGSASDLETSGLQEQRNHLQGKLSELQVEQT SLEPLQESPRPTGVWKSREVATEG IRGHRKMVLYTL-RAPR$_{76}$ (SEQ ID NO: 3).

Interestingly, these 3 polypeptides, proBNP(1-108), NT-proBNP(1-76) and BNP(1-32), have proved to be good markers of congestive heart failure in such a way that different assays with specific combinations of antibodies have been developed.

Indeed, as proBNP(1-108) has been recognised as circulating in the blood since the initial studies of Tateyama et al. (1992) *Biochemical and Biophysical Research Communications* 185: 760-767, different immunological assays for detecting proBNP(1-108) have been suggested. Patent application WO 99/13331 thus describes a sandwich assay of proBNP(1-108) with the aid of an antibody which recognises the 1-76 portion of proBNP(1-108) and an anti-BNP (1-32) antibody. This type of assay lacks sensitivity due to the binding, onto the solid phase (capture antibodies), of by-products of cleaved proBNP(1-108) having the epitope recognised by the capture antibody, that is to say, NT-proBNP(1-76) and the products resulting from the progressive cleavage thereof.

Application WO 2004/14952 describes the detection of proBNP(1-108) with the aid, on the one hand, of an antibody which recognises an epitope of the sequence RAPRSP, located at the hinge of NT-proBNP(1-76) and BNP(1-32) (also called hinge 76 antibody) and, on the other hand, an anti-BNP(1-32) antibody in such a way that, in this type of assay, the assay is specific to the prohormone only, i.e. there is no cross-reactivity with the two forms of NT-proBNP(1-76) and BNP(1-32).

With regard to the assay of NT-proBNP(1-76), application WO 93/24531 describes a method for in vitro diagnosis of congestive heart failure based on the detection of NT-proBNP(1-76). However, the method described in application WO 93/24531 does not appear to be easily carried out on NT-proBNP(1-76) in blood samples. Indeed, the only examples shown were carried out, not on human sera, but on standard ranges obtained using a synthetic peptide, the peptide NT-proBNP(47-64). In order to overcome this drawback, a highly sophisticated automated system has since proven to be necessary.

Finally, a plurality of assays of BNP(1-32) have been developed using various antibodies. For example, patent JP 2 676 114 B2 describes 2 monoclonal antibodies (KY-hBNPI and KY-hBNPII) which recognise the cyclic structure of BNP(1-32), with no other details.

In addition, patent application EP 542 255 describes a monoclonal antibody which recognises the histidine $H_{32}$, last amino acid of the C-terminal $K_{27}VLRRH_{32}$ epitope of BNP(1-32). Other epitopes present on BNP(1-32) are known: 3 epitopes of the sequence $1SPKMVQGSGC_{10}$ (SEQ ID NO: 22), $_5VQGSGCFGR_{13}$ (SEQ ID NO: 21), and $_{15}MDRISSSSGLG_{25}$ (SEQ ID NO: 23) are also described as being highly immunogenic in application WO 97/32900 and U.S. Pat. No. 6,162,902. Said documents also describe monospecific antibodies directed against these epitopes.

In 2005, the HyTest company (Turku, Finland) put various antibodies specific of BNP(1-32) on the market. As described in the article by Seferian et al. (2007) *Clinical Chemistry* 53:5, 866-873, some of these anti-BNP(1-32) antibodies target the 1-10, 11-22, 17-23 or 26-32 region of BNP(1-32). Among the 17 antibodies obtained by immunising Balb/c mice using the $_{11}FGRKMDRISSSS_{22}$ (SEQ ID NO: 61) peptide of BNP(1-32), only the 24C5 and the 26E2 monoclonal antibodies are described. However, their epitopes are not precisely characterised: it is only indicated that they are directed against the above mentioned sequence of amino acids 11 to 22 of BNP(1-32).

Patent application WO 2006/88700 describes another epitope present on BNP(1-32). It has the sequence of amino acids $R_{13}(K_{14})(M_{15})D_{16}R_{17}I_{18}$ (SEQ ID NO: 24), included in the amino acids 13-20 which form part of the cyclic structure of human BNP(1-32). This application also describes a monoclonal antibody, designated 3-631-436, which recognises this epitope specifically. The 4 amino acids $R_{13}$, $D_{16}$, $R_{17}$, and $I_{18}$ are described as being functionally significant for binding the 3-631-436 antibody to this epitope. The amino acids located upstream this epitope (such as phenylalanine $F_{11}$ and glycine $G_{12}$) are not mentioned.

One of the drawbacks of the BNP(1-32) hormone is that it is unstable in plasma and in serum. Indeed, protease-type enzymes seem to cleave BNP(1-32). For example, Shimizu et al. (2002) *Clinica Chimica Acta* 316: 129-135 report that the N-terminal part of BNP(1-32), more particularly the $Pro_2$-$Lys_3$ bond, would be cleaved by proteases, as well as the $Arg_{30}$-$Arg_{31}$ bond in the C-terminal position. Boerrigter et al. (2007) *Am. J. Physiol. Regul. Integr. Comp. Physiol.* 292: R897-90 and Hawkridge et al (2005) *Proc. Natl. Acad. Sci. USA*. 102:17442-7 have described, in particular, the degradation of BNP(1-32) in N-terminal position.

Likewise, some bond cleavages caused by endopeptidases have been reported (Davidson & Struthers (1994) *J. Hypertension* 13: 329-336). Therefore, the assay of BNP(1-32) calls for specific precautions (Davidson et al (1995) *Circulation* 91:1276-7; Gobinet-Georges et al. (2000) *Clin. Chem. Lab. Med.* 38:519-23), and implies a suitable choice of antibodies.

Recently, several teams have shown that natriuretic peptides could circulate in glycosylated and/or truncated form (Schellenberger (2006) *Arch. Biochem. Biophys.* 451: 160-6; Liang et al. (2007) *Journal of the American College of Cardiology* 49: 1071-8; Lam et al. (2007) *Journal of the American College of Cardiology* 49: 1193-292).

With regard to early diagnosis of congestive heart failure, ACSs, dyspnoea and other cardiovascular diseases as well as CVAs and associated pathologies, such as diabetis and kidney failure, there is always a need to improve the reagents and methods for detecting BNP(1-32) and proBNP (1-108), in particular taking into account the problem of the instability of BNP(1-32).

DESCRIPTION OF THE INVENTION

The present invention follows mainly from the entirely unexpected finding by the inventors of an unknown and unsuspected epitope which exists in the human BNP(1-32) molecule and a specific monoclonal antibody which recognises said epitope. Contrary to all expectations, they discovered that the sequence $F_{11}GRKMDR_{17}$ (SEQ ID NO: 51) of BNP(1-32) constitutes a beneficial epitope for generating antibodies which recognise the cyclic structure (amino acids 10-26) of BNP(1-32) and they obtained a monoclonal antibody, called 20G7, which specifically recognises said $F_{11}G_{12}RK_{14}MDR_{17}$ (SEQ ID NO: 51) epitope. In other words, the 20G7 antibody is a monoclonal antibody specific of the $F_{11}GRKMDR_{17}$ (SEQ ID NO: 51) epitope of BNP (1-32).

The present invention also provides an immunoassay method for detecting BNP(1-32) and proBNP(1-108) as well as circulating fragments thereof using the 20G7 monoclonal antibody and reagents containing said antibody.

Indeed, the inventors noticed that, while synthesizing peptides located in the cyclic region (amino acids 10-26) of human BNP(1-32) and immunising mice with said peptides, some resulting antibodies only reacted with peptides of this type if said peptides contained phenylalanine $F_{11}$ residues, lysine $K_{14}$ and Arginine $R_{17}$ and that isoleucine $I_{18}$, which was particularly significant in the epitope described in the international application WO2006/88700, did not belong to the epitope according to the present invention.

For example, the inventors immunised some mice with the TGCFGRKMDRISTSTAIGCKVL (SEQ ID NO: 4) peptide and others with the SGC YGRKMDRISTSTAIGCKVL (SEQ ID NO: 5) peptide. They observed that the immune response to BNP(1-32) was much greater in the mice immunised with the TGC FGRKMDRISTSTAIGCKVL (SEQ ID NO: 4) peptide than in the mice immunised with the SGC YGRKMDRISTSTAIGCKVL (SEQ ID NO: 5) peptide. It should be noted that, in both cases, cysteines are presented in oxidised form via an intrachain disulphide bond.

After lymphocytic fusion of immunised mice spleen cells with myeloma cells, the inventors were thus able to produce different hybrid clones. In particular, they obtained a monoclonal antibody, called 20G7-15/03/2007 (hereinafter, referred to as "20G7" for convenience), which only recognises those peptides of BNP(1-32) and proBNP(1-108) which contain the residues phenylalanine $F_{11}$, lysine $K_{14}$ and arginine $R_{17}$. In fact, these amino acids $F_{11}$, $K_{14}$ and $R_{17}$ have proven to be important for optimal binding of the 20G7 monoclonal antibody to BNP(1-32) and to proBNP(1-108) as well as to respective fragments thereof.

The hybridoma which secretes the 20G7-15/03/2007 (20G7) monoclonal antibody was deposited on Apr. 13, 2007 by Bio-Rad at the CNCM (Collection Nationale de Cultures de Microorganismes, Institut Pasteur, 25, rue du Docteur Roux, 75 724 Paris Cedex 15, France) under registration number CNCM I-3746.

Surprisingly and unexpectedly, the inventors observed with the 20G7 antibody that, as soon as the residues $F_{11}$, $K_{14}$ and $R_{17}$ were substituted by an alanine, either individually or jointly, the antigenic reactivity of the peptide, compared to that of the natural SGCFGRKMDRISSSSGLGCKVL (SEQ ID NO: 6) peptide, was considerably affected, whereas substituting other amino acids of the epitope had almost no effect on the antigenic reactivity of the peptide. Also, an in-depth study on the 20G7 antibody has shown that it recognises the $F_{11}GRKMDR_{17}$ (SEQ ID NO: 51) epitope, but does not recognise the $A_{11}GRKMDR_{17}$ (SEQ ID NO: 62) sequence nor the $GRKMDR_{17}I_{18}$ (SEQ ID NO: 52) sequence, nor the $C_{10}F_{11}GRKMD$ (SEQ ID NO: 50) sequence.

The 20G7 monoclonal antibody thus recognises the $F_{11}GRKMDR_{17}$ (SEQ ID NO: 51) epitopic sequence of BNP(1-32), but does not substantially recognise the above mentioned VQGSGCFGR (SEQ ID NO: 21), SPKM-VQGSGC (SEQ ID NO: 22), and MDRISSSSGLG (SEQ ID NO: 23)) epitopes of application WO 97/32900, nor the R(K)(M)DRI (SEQ ID NO: 24) epitope of application WO2006/88700.

The present invention therefore relates to a polypeptide carrying a human BNP(1-32) epitope having the formula (I):

$$a_1\text{-}R_1\text{-}X_1\text{-FGRKMDR-}X_2\text{-}R_2\text{-}a_2(\text{SEQ ID NO: 51}) \quad (1)$$

wherein $a_1$ may be H or represent a functional group or chemical group selected from a thiol, alcohol, aminoxy, primary amine or secondary amine functional group, an amino carboxyl group, a biotinyl group and an acetyl group;

$a_2$ may represent an OH, $NH_2$ functional group or an alcoxyl group (as will be clear for the man skilled in the art $a_2$ is attached to the carbonyl (—CO—) moiety of the acidic function of the last amino acid of the polypeptide);

$X_1$ is absent or present and when present is selected among C and GC;

$X_2$ is absent or present and when present is selected among I and IS;

$R_1$ and $R_2$, which may be the same or different, absent or present, represent any amino acid or a peptide chain of 2 to 15 amino acids, provided that said polypeptide of formula (I) does not include any portion of human BNP(1-32) of more than 11 amino acids including the sequence GCFGRKM-DRIS (SEQ ID NO: 63).

As an equivalent alternative, formula (I) can also be defined as follows:

$$a_1\text{-}(R_1)\text{-}(G)\text{-}(C)\text{-FGRKMDR-}(I)\text{-}(S)\text{-}(R_2)\text{-}a_2(\text{SEQ ID NO: 51})$$

wherein $a_1$, $a_2$, $R_1$ and $R_2$ are as defined above.

"Epitope" or "epitopic site" means an amino acid sequence which is recognised by at least one antibody and allows the antibody to bind specifically to said amino acid sequence.

In a preferred embodiment, $R_1$ and $R_2$ may be coupled to carrier molecules, reagents or marker molecules.

In another preferred embodiment, said polypeptide is selected in the group consisting of $a_1$-SGCFGRKMDR-$a_2$ (SEQ ID NO: 33), $a_1$-GCFGRKMDRI-$a_2$ (SEQ ID NO: 34), $a_1$-CFGRKMDRIS-$a_2$ (SEQ ID NO: 35) and $a_1$-FGRKM-DRISS-$a_2$ (SEQ ID NO: 36), where $a_1$ and $a_2$ are as defined above.

In another preferred embodiment, the polypeptide as defined above corresponds to formula (II):

$$a_1\text{-FGRKMDR-}a_2(\text{SEQ ID NO: 51}) \quad (II)$$

wherein $a_1$ and $a_2$ are as defined above.

The present invention also relates to the use of a polypeptide as defined above, for the preparation of ligands directed against human BNP(1-32) or human proBNP(1-108) as well as the respective fragments thereof comprising the sequence FGRKMDR (SEQ ID NO: 51).

"Fragment of proBNP(1-108)" according to the invention means any fragment which is smaller than proBNP(1-108), including, in particular, BNP(1-32). For example, the proBNP(3-108) fragment, as described in Lam et al. (2007) *J. Am. Coll. Cardiol.* 49:1193-1202 and produced by cleavage by a dipeptidase. The term "fragment of proBNP(1-108)" according to the invention also includes any polypeptide having been subjected to at least one post-translational modification of proBNP(1-108), such as phosphorylation, glycosylation or the like. For example, Schellenberger et al. (2006) *Arch. Biochem. Biophys.* 51:160-6 have shown that proBNP(1-108) is a glycoprotein which is O-glycosylated either entirely or in part.

"Fragment of BNP(1-32)" according to the invention means any fragment which is smaller than BNP(1-32). In this case also, degradation of BNP(1-32) has already been reported in the literature: for example, the BNP(3-32) fragment has been described by Lam et al (supra) and by Hawkridge et al. (2005) *Proc. Natl. Acad. Sci. USA* 102: 17442-7.

The terms "proBNP(1-108)" and "BNP(1-32)" as well as "fragment of proBNP(1-108)" and "fragment of BNP(1-32)" also include any polypeptide having been subjected to at least one post-translational modification, such as phosphorylation, glycosylation or the like. For example, Schellenberger et al. (2006) *Arch. Biochem. Biophys.* 51:160-6 have shown that proBNP(1-108) is a glycoprotein which is O-glycosylated either entirely or in part.

"Ligands directed against human BNP(1-32) or human proBNP(1-108) as well as respective fragments thereof comprising the sequence FGRKMDR" (SEQ ID NO: 51) refers to any molecule able to bind specifically to human BNP(1-32), to human proBNP(1-108) or to fragments thereof.

The term "specific", when it refers to recognition of a ligand or binding of a ligand to a target, means that the ligand interacts with the target without interacting substantially with another target which does not structurally resemble the target. "Specific" recognition of the FGRK-MDR (SEQ ID NO: 51) epitope means that the interaction of the ligand with a target comprising the epitope does not substantially involve antigenic determinants, in particular amino acids, other than those of the epitope. In particular, this means that the ligand is able to bind a sequence of amino acids of the BNP(1-32) and/or proBNP(1-108) sequence as well as respective fragments thereof comprising the amino acids comprising the FGRKMDR (SEQ ID NO: 51) epitope, but is unable to bind a sequence of amino acids of the BNP(1-32) and/or proBNP(1-108) sequence which does not comprise the FGRKMDR (SEQ ID NO: 51) epitope in its entirety.

In addition, an amino acid present in an epitope is said to be "critical" as soon as its substitution by an alanine leads to a reduction of at least 50% in the antigenicity of said epitope, according to Laune et al. (2002) *Journal of Immunological Methods* 267:53-70.

Moreover, an amino acid present in an epitope is said to be "essential" as soon as its substitution by an alanine leads to a reduction of at least 80% in the antigenicity of said epitope.

Preferably, a ligand which specifically recognises the FGRKMDR (SEQ ID NO: 51) epitope according to the invention does not interact substantially with peptides having the sequence VQGSGCFGR (SEQ ID NO: 21), SPKMVQGSGC (SEQ ID NO: 22), MDRISSSSGLG (SEQ ID NO: 23), RKMDRI (SEQ ID NO: 24) and RKMDRISS (SEQ ID NO: 25).

The expression "does not interact substantially with peptides having the sequence VQGSGCFGR (SEQ ID NO: 21), SPKMVQGSGC (SEQ ID NO: 22), MDRISSSSGLG (SEQ ID NO: 23), RKMDRI (SEQ ID NO: 24) and RKMDRISS (SEQ ID NO: 25)" means that the ligand has a cross reaction with one or other of these sequences of less than 20° A), preferably less than 10%, more preferably less than 5%, particularly preferably less than 2%.

Within the scope of specific recognition of a target, binding constants greater than $10^6$ $M^{-1}$ are preferred, binding constants greater than $10^8$ $M^{-1}$ are more preferred and binding constants greater than $10^{10}$ $M^{-1}$ are particularly preferred.

Preferably, the residues $F_{11}$, $K_{14}$ and $R_{17}$ are also essential for binding a ligand according to the invention to the epitope, since their substitution by an alanine is characterised by a loss of 82%, 95% and 85% respectively in the binding of the monoclonal antibody produced by the hybridoma deposited on Apr. 13, 2007 by Bio-Rad at the CNCM (Collection Nationale de Cultures de Microorganismes, Institut Pasteur, 25, rue du Docteur Roux, 75 724 Paris Cedex 15, France) under registration number CNCM I-3746, to the epitopic peptide.

Preferably, the ligand is selected from the group constituted by an antibody or a fragment of said antibody which recognises the epitope, an aptamer, and a polypeptide which specifically recognises the epitope obtainable by phage display.

In this context, the term "antibody" refers to any polyclonal or monoclonal antibody.

The fragments scFv, Fab, Fab', F(ab')$_2$, as well as camelids single-chain antibodies are examples of antibody fragments which recognise the epitope.

The "aptamers" are well-known by the one skilled in the art. Aptamers are compounds of a nucleotide, in particular a ribonucleotide or desoxyribonucleotide, or a peptide nature able to bind specifically to a target, in particular a protein target. The aptamers of a nucleotide nature and the production thereof are described, in particular, by Ellington et al. (1990) *Nature* 346:818-22 and Bock et al. (1992) *Nature* 355:564-6. The aptamers of a peptide nature and the production thereof are described, in particular, by Hoppe-Seyler et al. (2000) *J. Mol Med.* 78:426-30.

"Phage display" denotes a technique for selecting polypeptide ligands expressed on the capsid of a bacteriophage and encoded by a nucleic sequence inserted into the capsid encoding gene. This method is well known by the one skilled in the art and is described, in particular, by Scott & Smith (1990) Science 249:386-390, and Marks et al. (1991) *J. Mol. Biol.* 222:581-597. Preferably, the polypeptide obtainable by phage display is an scFv-type polypeptide (single-chain variable fragment). This technique is described, in particular, by Winter et al. (1994) *Annu. Rev. Immunol.* 12:433-455.

The ligands may also be obtained by chemical synthesis or by genetic engineering.

Preferably, the polypeptides as defined above are used to prepare antibodies, in particular monoclonal antibodies.

In this context, the invention also relates to use of a polypeptide as defined above for the preparation of a hybridoma which secretes a monoclonal antibody directed against human BNP(1-32) or human proBNP(1-108) as well as the respective fragments thereof comprising the sequence FGRKMDR (SEQ ID NO: 51).

The invention thus also relates to a method for preparing a hybridoma which secretes a monoclonal antibody directed against human BNP(1-32) or human proBNP(1-108) as well as the respective fragments thereof comprising the sequence FGRKMDR (SEQ ID NO: 51), wherein:

samples of lymphocytes secreting immunoglobulins are taken from an animal, such as a mouse, rabbit or rat, immunised with a polypeptide as defined above, the lymphocytes are then fused with myeloma cells, such as Sp2 myeloma cells (ATCC CRL-1581), in order to obtain a hybridoma.

The present invention also relates to a hybridoma obtainable by the method for preparing a hydridoma defined above.

More particularly, the present invention relates to the hybridoma deposited on Apr. 13, 2007 at the CNCM (Collection Nationale de Cultures de Microorganismes, Institut Pasteur, 25, rue du Docteur Roux, 75 724 Paris Cedex 15, France) under registration number CNCM I-3746.

Generally, the methodology used to obtain hybridomas and monoclonal antibodies may follow the conventional method of lymphocyte fusion and hybridoma culture described by Köhler & Milstein (1975) Nature 256:495-497. Other methods for preparing monoclonal antibodies are also known (e.g., Harlow et al, ed. 1988 "Antibodies: a laboratory manual").

Alternative methods to this conventional method also exist. Monoclonal antibodies can be produced, for example, by expressing a nucleic acid cloned from a hybridoma.

The present invention also relates to a ligand specific of an epitope of the sequence FGRKMDR (SEQ ID NO: 51).

Preferably, the ligand is selected from the group constituted by an antibody or a fragment of said antibody which recognises the epitope, an aptamer, and a polypeptide which specifically recognises the epitope obtained by phage display.

More preferably, the ligand is constituted by an antibody which specifically recognises an epitope of the sequence FGRKMDR (SEQ ID NO: 51), or a fragment of said antibody which specifically recognises the epitope. Even more preferably, the ligand is constituted by a monoclonal antibody, in particular a monoclonal antibody produced by a hybridoma as defined above.

The invention thus relates, in particular, to a ligand as defined above, constituted by the monoclonal antibody produced by the hybridoma deposited on Apr. 13, 2007 at the CNCM (Collection Nationale de Cultures de Microorganismes, Institut Pasteur, 25, rue du Docteur Roux, 75 724 Paris Cedex 15, France) under registration number CNCM I-3746.

The invention further more particularly relates to a ligand as defined above harbouring at least one Complementary Determining Region (CDR), in particular all the CDR, of the above-defined ligand constituted by the monoclonal antibody produced by the hybridoma deposited on Apr. 13, 2007 at the CNCM (Collection Nationale de Cultures de Microorganismes, Institut Pasteur, 25, rue du Docteur Roux, 75 724 Paris Cedex 15, France) under registration number CNCM I-3746. CDR and methods for transferring a CDR from an antibody to a ligand, preferably another antibody, are well known to the man skilled in the art and are notably described e.g. in Nicaise et al. (2004) *Protein Science* 13:1882-1891 or Kettleborough et al. (1991) *Protein Engineering* 4:773-783.

In addition, the ligands as defined above may be coupled to carrier molecules, reagents or labelled molecules.

The present invention also relates to a ligand as defined above for detecting, in a biological sample, human BNP(1-32) or human proBNP(1-108) as well as the respective fragments thereof comprising the sequence FGRKMDR (SEQ ID NO: 51).

In fact, the present invention also relates to a method for detecting, in a biological sample, human BNP(1-32) or human proBNP(1-108) as well as respective fragments thereof containing the sequence FGRKMDR (SEQ ID NO: 51), comprising:
1) contacting the biological sample with at least one ligand as defined above, preferably under conditions allowing the formation of antigen-ligand complexes, and
2) detecting any complexes which may have formed.

In the context of the invention, a "biological sample" or even a "biological fluid sample" is preferably constituted by a biological liquid, such as blood, plasma, serum, cerebrospinal fluid, saliva, urina and lacrima, etc. (see e.g. Michielsen et al., (2008) *Ann Clin Biochem* 45:389-94; Cortes et al., (2006) *Eur J Heart Fail* 8:621-7; Kirchhoff et al., (2006) *J Neurotrauma* 23:943-9; Kaneko et al., (1993) *Brain Res* 612:104-9). As it is meant in this case, the term "biological sample" includes both the sample as taken and the sample which has been subjected to various treatments, in particular to render it suitable for use in the processes and methods according to the invention.

In a preferred embodiment, the above detection method comprises at least one additional step of contacting the biological sample with at least one additional ligand specific of human BNP(1-32) or human proBNP(1-108) and of the respective fragments thereof, with has a different specificity from that of the ligand according to the invention.

Preferably, the additional ligand is an antibody.

The present invention also relates to a method of diagnosis, prognosis, risk stratification or therapeutic follow-up of at least one cardiac and/or vascular pathology in an individual, comprising the following steps of:
1) contacting a biological sample from the individual with at least one ligand as defined above, preferably under conditions allowing the formation of antigen-ligand complexes,
2) detecting any complex which may have formed, and,
3) based on the result of the detection in step 2, determining a diagnosis, a prognosis, a risk of the development or therapeutic follow-up of the pathology in the individual.

In a particular embodiment, the method defined above comprises at least one additional step of contacting the biological sample with at least one additional ligand specific of human BNP(1-32), or a human proBNP(1-108) derivative, which has a different specificity to that of the ligand according to the invention.

Preferably, the additional ligand is an antibody.

Preferably, the pathology is selected from the group constituted of:
congestive heart failure,
acute coronary syndrome,
cerebrovascular accident,
kidney failure,
dyspnea,
high blood pressure,
atheromatous plaque rupture,
patent ductus arteriosus in premature newborns, and/or diabetis.

"Congestive heart failure" means the pathological state in which an anomaly of the cardiac function is responsible for the heart being unable to pump blood sufficiently to satisfy the metabolic needs of the organism and/or in which the heart fulfils needs but with abnormally high filling pressures. In particular, it may relate to a left and/or right ventricular failure.

"Acute Coronary Syndromes" denotes two categories in particular:
acute coronary insufficiency accompanied by a persistent upslope [i.e. elevation] of the ST segment revealing the formation of a Q-wave transmural infarction corresponding generally to an acute total coronary occlusion, and
acute coronary insufficiency with no upslope [i.e. with no elevation] of the ST segment corresponding to non-Q-wave infarction, also known as unstable anginas which correspond to plaque ruptures and incomplete thromboses and require different treatment.

"Dyspnea" means the pathological state characterised by breathing difficulties accompanied by feelings of obstruction or tightness. It is an extremely common symptom which may be due to several causes. Only a methodical approach enables appropriate treatment.

According to the definition of the World Health Organisation, "cerebrovascular accident" or "CVA" or "stroke" or "apoplexy" means the pathological state characterised by the rapid development of localised or global clinical signs of cerebral dysfunction accompanied with symptoms lasting more than 24 hours, which may result in death, with no apparent cause other than a vascular origin.

The process and the method above may be carried out in accordance with various formats well-known to the one skilled in the art, for example in solid or homogeneous phase, in one or two steps, by a sandwich method or by a competitive method.

Preferably, the sandwich method in solid phase between 2 ligands (preferably antibodies), one being a capture ligand and the other being a detection ligand, will be used. This type of immunoassay is particularly well-known to the one skilled in the art. For example, the article by Seferian et al. (2007) *Clin. Chem.* 53:866-873 gives an example of a sandwich immunoassay (or immunometric assay at 2 sites) for assaying BNP(1-32) and proBNP(1-108), each time using a pair of antibodies (an antibody immobilised in solid phase and an labelled antibody in detection).

"Capture ligand" means a ligand capable of binding the BNP(1-32) and/or proBNP(1-108) antigen, as well as the respective fragments thereof, present in the biological sample.

The presence of the antigen in the biological sample is revealed by detection means, in particular a "detection ligand". A detection ligand, which is labelled, is able to bind to the captured antigen, by recognising an epitopic site which is different from that recognised by the capture ligand.

The term "labelled" refers both to a direct labelling and to an indirect labelling (for example, by means of other ligands, themselves directly labelled, or using reagents of a labelled "affinity pair", such as, but not exclusively, the labelled avidin-biotin pair, etc.).

In the case of the sandwich method, the capture ligand is preferably selected in such a way that it specifically recognises an epitope on the natural antigen of the patient, whilst the detection ligand is selected preferably in such a way that it specifically recognises another epitope on the natural antigen of the patient.

Preferably, the capture ligand is immobilised on a solid phase. By way of non-limiting examples of solid phase, microplates could be used, in particular polystyrene microplates, such as those sold by Nunc, Denmark. Solid particles or beads, paramagnetic beads, such as those produced by Dynal, Merck-Eurolab (France) (under the trademark Estapor™) and Polymer Laboratories, or even polystyrene or polypropylene test tubes, glass, plastic or silicon chips, etc. may also be used.

ELISA assays, radioimmunoassays, or any other detection method may be used to reveal the presence of formed antigen-antibody complexes. Thus, different types of labelling of ligands in particular of antibodies, are possible (radioactive, enzymatic, fluorescent, etc.).

The detection may also be carried out by new methods based on mass accumulation, such as surface plasmon resonance (SPR), by piezo-electric detection, but also by mass spectrometry or any other methods defined as enabling the study of a ligand-antigen-type interaction in the absence of a second labelled ligand.

A preferred implementation of the above process or method consists in using a ligand as defined above immobilised on a solid phase in combination with at least one monoclonal or polyclonal antibody directed against the N-terminal portion of BNP(1-32), present in a labelled form.

Another preferred implementation of the above process or method consists in using a ligand as defined above immobilised on a solid phase in combination with at least one monoclonal or polyclonal antibody directed against the C-terminal portion of BNP(1-32), such as the 50B7 antibody, (specific of the 26-32 peptide of BNP(1-32)), available from HyTest, present in a labelled form.

Alternatively, according to yet another preferred implementation of the above method or process, a ligand as defined above may be used, in a labelled form, in combination with at least one monoclonal or polyclonal antibody directed against the N-terminal or C-terminal portion of BNP(1-32), present in an immobilised form on a solid phase.

A preferred implementation of the above method or process consists in using a ligand as defined above immobilised on a solid phase in combination with at least one monoclonal or polyclonal antibody directed against the N-terminal portion of NT-proBNP(1-108), such as the 16F3 antibody, (specific of the 13-20 peptide of NT-proBNP), available from HyTest, present a labelled form.

Alternatively, a preferred implementation of the above method or process consists in using a ligand as defined above a labelled form in combination with at least one monoclonal or polyclonal antibody directed against the N-terminal portion of proBNP(1-108), such as the 16F3 antibody, (specific of the 13-20 peptide of NT-proBNP), available from HyTest, present in an immobilised form on a solid phase.

Another preferred implementation of the above method or process consists in using a ligand as defined above immobilised on a solid phase in combination with a monoclonal antibody directed against the RAPR$_{76}$S$_{77}$P (SEQ ID NO: 55) sequence of proBNP(1-108) (such as the one described in patent application WO2004/14952, or in Giuliani et al. (2006) *Clin. Chem.* 52:1054-1061), present in a labelled form.

Alternatively, a preferred implementation of the above method or process consists in using a ligand as defined above in a labelled form in combination with a monoclonal antibody directed against the RAPR$_{76}$S$_{77}$P (SEQ ID NO: 55) sequence of proBNP(1-108) (such as the one described in patent application WO2004/14952, or in Giuliani et al. (2006) *Clin. Chem.* 52:1054-1061), present in an immobilised form on a solid phase.

The present invention also relates to a multiepitopic calibrator having the following general formula (III):

$$t_1\text{-}E_1\text{-}L_1\text{-}E_2[\text{-}L_{k-1}\text{-}E_k]_n\text{-}t_2 \tag{III}$$

wherein:

n is an integer between 0 and 8;

k is an integer between 3 and n+2 when n>0;

$E_1$, $E_2$, and $E_k$ are different from one another, one representing a $R_1$-$X_1$-FGRKMDR-$X_2$-$R_2$ (SEQ ID NO: 51) peptide sequence, wherein $X_1$, $X_2$, $R_1$ and $R_2$ are as defined above, and the others representing a sequence of 3 to 15 amino acids selected from the sequence of human proBNP (1-108);

$t_1$ represents a hydrogen atom, an acetyl group, a peptide sequence of 1 to 10 amino acids, a peptide sequence of 1 to 10 N-α acetylated amino acids, a biotinyl or biocytinyl group, a peptide sequence of 1 to 10 amino acids carrying a biotinyl or biocytinyl radical, or a linear amino alkyl ($C_1$-$C_{10}$) carbonyl chain;

$t_2$ represents a hydroxyl radical, an amino radical, a peptide sequence of 1 to 10 amino acids, a peptide sequence of 1 to 10 amino acids carrying a terminal amino group, or a linear or branched amino alkyl ($C_1$-$C_{10}$) carbonyl chain (as will be clear for the man skilled in the art $t_2$ is attached to the carbonyl (—CO—) moiety of the acidic function of the last amino acid of the $E_n$ peptide chain);

$L_1$ and $L_k$, which may be the same or different, represent a binding group of peptide chains.

Preferably, the above multiepitopic calibrator corresponds to the following general formula (IV):

$$t_1\text{-}E_1\text{-}L_1\text{-}E_2\text{-}L_2\text{-}E_3\text{-}t_2 \tag{IV}$$

wherein $E_1$, $E_2$, $E_3$, $L_1$, $L_2$, $t_1$ and $t_2$ are as defined above.

Preferably, the above multiepitopic calibrator corresponds to the following general formula (V):

$$t_1\text{-}E_1\text{-}L_1\text{-}E_2\text{-}t_2 \tag{V}$$

wherein $E_1$, $E_2$, $L_1$, $t_1$, and $t_2$, are as defined above.

The above standards (or calibrators) are used to establish standard curves for the assays of BNP(1-32), proBNP(1-108) and/or one of the aforementioned fragments thereof. One advantage of said calibrators is, in particular, their stability.

Preferably, when used for assaying BNP(1-32), a biepitopic standard according to the invention comprises the FGRKMDR (SEQ ID NO: 51) epitope according to the invention and another, different epitope which is selected from the sequence of amino acids 77-108 of proBNP(1-108).

Preferably, when used for assaying proBNP(1-108), a biepitopic calibrator according to the invention comprises the FGRKMDR (SEQ ID NO: 51) epitope according to the invention and another, different epitope which is selected from the sequence of amino acids 1-76 of proBNP(1-108) so as to ensure the specificity of the proBNP(1-108).

Preferably, when used for assaying BNP(1-32), a triepitopic calibrator according to the invention comprises the $R_1$-$X_1$-FGRKMDR-$X_2$-$R_2$ (SEQ ID NO: 51) epitope according to the invention and two other, different epitopes which are selected from the sequence of amino acids 77-108 of proBNP(1-108).

Preferably, when used for assaying proBNP(1-108), a triepitopic calibrator according to the invention comprises the $R_1$-$X_1$-FGRKMDR-$X_2$-$R_2$ (SEQ ID NO: 51) epitope according to the invention and two other, different epitopes which are selected from the sequence of amino acids of 1-108 proBNP(1-108).

Preferably, in the above calibrator, $R_1$-$X_1$-FGRKMDR-$X_2$-$R_2$ (SEQ ID NO: 51) represents a peptide sequence selected from the group constituted of SGCFGRKMDR (SEQ ID NO:33), GCFGRKMDRI (SEQ ID NO:34), CFGRKMDRIS (SEQ ID NO:35), FGRKMDRISS (SEQ ID NO:36), FGRKMDR (SEQ ID NO:8), SFGRKMDRISS (SEQ ID NO: 64), and CFGRKMDRISSSSGLGCK (SEQ ID NO: 65).

Preferably, the sequences different of $R_1$-$X_1$-FGRKMDR-$X_2$-$R_2$ (SEQ ID NO: 51) are selected from the group constituted by PRSPKMVQG (SEQ ID NO: 56), APRSPKMV (SEQ ID NO: 57), SGLGCKVL (SEQ ID NO: 58), SPKMVQGSG (SEQ ID NO: 59), YTLRAPRSPKMVG (SEQ ID NO: 60), YTLRAPRSPKMV (SEQ ID NO: 66), YTLRAPRSPKMVQG (SEQ ID NO: 67), SGLGCKVLRRH (SEQ ID NO: 68), and SGLGCKVLR (SEQ ID NO: 69).

Preferably, the multiepitopic calibrators according to the invention are selected from the group consisting of the multiepitopic calibrators defined by the following formulae:

Ac-YTLRAPRSPKMV-$L_1$-SFGRKMDRISS-$NH_2$
(SEQ ID NO: 66 and SEQ ID NO: 64);

Ac-YTLRAPRSPKMV-$L_1$-CFGRKMDRISSSSGL-GCK-$NH_2$(SEQ ID NO: 66 and SEQ ID NO: 65);

Ac-YTLRAPRSPKMVQG-$L_1$-FGRKMDR-$NH_2$;
(SEQ ID NO: 66 and SEQ ID NO: 51)

Ac-FGRKMDR-$L_1$-SGLGC*KVLRRH-OH;(SEQ ID NO: 51 and SEQ ID NO: 68)

Ac-FGRKMDR-$L_1$-SGLGC*KVLR-$NH_2$;(SEQ ID NO: 51 and SEQ ID NO: 69)

Ac-SPKMVQGSG-$L_1$-FGRKMDR-$NH_2$;(SEQ ID NO: 59 and SEQ ID NO: 51)

Ac-YTLRAPRSPKMV-$L_1$-FGRKMDR-$L_2$-SGLGC*KVLRRH-OH;(SEQ ID NO: 66 and SEQ ID NO: 51 and SEQ ID NO: 68)

and Ac-YTLRAPRSPKMV-$L_1$-FGRKMDR-$L_2$-SGLGC*KVLR-$NH_2$(SEQ ID NO: 66 and SEQ ID NO: 51 and SEQ ID NO: 69);

wherein Ac represents an acetyl group, and C* represents an acetamidomethyl-blocked cysteine.

Preferably, $L_1$ and $L_2$ represent:

—NH—$(CH_2)_5$—CO—.

This group may, in particular, derive from the coupling agent known as hexanoic amino acid.

When $E_1$, $E_2$ and $E_3$ are present, the calibrator is said to be triepitopic, when only $E_1$ and $E_2$ are present, then the calibrator is said to be biepitopic.

Moreover, the present invention also relates to a kit for detecting human BNP(1-32) or human proBNP(1-108) as well as the respective fragments thereof comprising the sequence FGRKMDR (SEQ ID NO: 51), comprising at least:
- a ligand as defined above; and
- a multiepitopic calibrator as defined above and/or a polypeptide as defined above.

In a particular embodiment, the above kit also comprises a positive biological control sample.

Preferably, the kit according to the invention comprises at least the monoclonal antibody produced by the hybridoma deposited on Apr. 13, 2007 at the CNCM (Collection Nationale de Cultures de Microorganismes, Institut Pasteur, 25, rue du Docteur Roux, 75 724 Paris Cedex 15, France) under registration number CNCM I-3746.

The following examples and figures illustrate the invention, without limiting it.

EXAMPLES

Example 1

Peptide Synthesis

Figure 1:
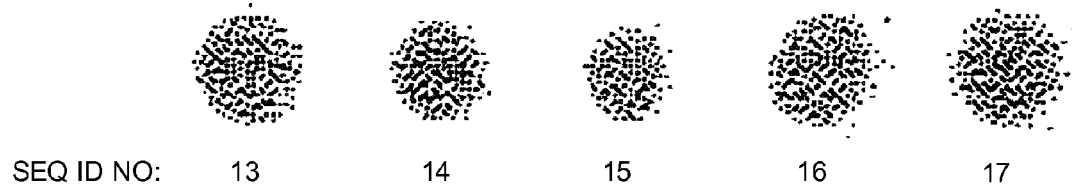
FIG. 1 shows the reactivity of the 20G7 antibody with immobilised pentadecapeptides representing the sequence of BNP(1-32) (from left to right, SEQ ID NO: 13, SEQ ID NO: 14, SEQ ID NO: 15, SEQ ID NO: 16 and SEQ ID NO: 17), synthesized by the Spot technique.

Materials and Methods:

Synthetic peptides were prepared by standard methods which are well known to the one skilled in the art. An example of this method is Merrifield synthesis, which is advantageous due to the fact that it can be implemented easily (Merrifield, (1963); R. C. Sheppard (1971); Atherton et al. (1989)). "Pioneer" synthesisers from Perspective, or the "433A" synthesiser from ABI may be used as the automatic synthesiser. The peptides may also be obtained by homogenous phase synthesis.

The following syntheses were carried out in a Pioneer synthesiser using "Fmoc" chemistry (9-fluorenylmethyloxy-carbonyl): in each step, the reagents (that is to say the protected amino acid and the coupling activators (TBTU(2-(1H-benzotriazol-1-yl)-1,1,3,3-tetramethyluronium tetra-fluoroborate)/HOBt (N-hydroxybenzotriazole)) were added in excess (in a "moles of reagent/moles of groups which can be substituted on the resin" ratio=5). At the end of the synthesis process, the peptide was separated from the resin by a trifluoroacetic acid solution (reagent K). The peptide was then precipitated in a cooled ether solution, lyophilised and then subsequently purified by HPLC.

In this way, the inventors synthesised peptides containing the following amino acid sequences:

```
SEQ ID NO: 4:    Ac-TGCFGRKMDRISTSTAIGCKVLCys-CONH2,

SEQ ID NO: 5:    5:Ac-SGCYGRKMDRISTSTAIGCKVL-Cy-
                 sCONH2

SEQ ID NO: 6:    Ac-SGCFGRKMDRISSSSGLGCKVL-CysCONH2

SEQ ID NO: 7:    Ac-SGCFGRKMDRIATSTAIGCKVL-CysCONH2

SEQ ID NO: 8:    Ac-FGRKMDR-CONH2

SEQ ID NO: 9:    Ac-GRKMDR-CONH2

SEQ ID NO: 10:   Ac-FGRKMD-CONH2

SEQ ID NO: 11:   Ac-RKMDRI-CONH2
```

Example 2

Immunogen Preparation: Coupling of a Peptide to a Carrier Protein for Immunisation In order to immunise mice with these peptides, it is necessary to couple said peptides to a carrier protein such as KLH (keyhole limpet haemocyanin), thyroglobulin, or BSA (bovine serum albumin), via different functional groups (thiol, amine, aldehyde, etc.) so as to render the peptide more immunogenic. The coupling reagent used to bind the peptide to the protein may be heterobifunctional or homobifunctional. The most frequently used reagents are BS3, sSMCC, SPDP, glutaraldehyde, etc.

The coupling method used involved the bifunctional sSMCC (Pierce, #22322) molecule, having an NHS ester functional group and a maleimide group as the chemical coupling agent, and KLH (Pierce, #77600) as the carrier protein.

2-a. KLH Activation

Method:

20 mg of KLH were solubilised in 2 ml of phosphate buffered saline (20 mM phosphate, 0.9 M NaCl pH 7.2) in order to obtain a final concentration of 10 mg/ml (do not vortex). In parallel, 4 mg of sSMCC were solubilised with 400 µl of water for injection to obtain a final concentration of 10 mg/ml. 2 ml of KLH (20 mg) were subsequently mixed with 200 µl of sSMCC (2 mg), and the mixture was incubated for 1 hour at room temperature (20° C.) whilst being stirred slowly (20 revolutions per min).

2-b. Desalting the Activated KLH:

Method:

A PD10 Sephadex™ G-25m column (Ge healthcare, USA, ref: 17-0851-01) was equilibrated with phosphate buffered saline (20 mM phosphate, 0.9 M NaCl pH 7.2, 100 mM EDTA). The 2 ml of activated KLH were deposited on the column, and the elution was subsequently started with 3.5 ml of 20 mM PBS buffer supplemented with 0.9 M NaCl, pH 7.2 and 100 mM EDTA; 500 µl fractions were collected. The optical density (OD) was measured at 280 nm for each fraction diluted to ½5th and the fractions containing the activated KLH were then identified and measured in accordance with the Beer-Lambert law: OD=εCl: wherein OD is the optical density $\epsilon$=1.499, C is the concentration and I=1 cm, the concentration of the activated KLH may be determined and is reduced to 7.4 mg/ml in phosphate buffered saline.

2-c. Coupling of the Peptide to the Activated KLH

Method:

10 mg of lyophilised peptide were solubilised in 1 ml of Milli-Q water, which was degassed in an ultrasonic disintegrator to obtain a final concentration of 10 mg/ml, and were then mixed with 7.4 mg of activated KLH (i.e. 1 ml of the solution obtained in 2-b.). This mixture was left to incubate for 2 hours at room temperature (20° C.) whilst being stirred slowly (20 rpm). A solution of cysteine at a concentration of 5 mg/ml in a 20 mM PBS buffer+0.9 M NaCl pH 7.2 was subsequently introduced to obtain a final concentration of 1 mM in the peptide/KLH solution, and the entire mixture was left to incubate for 20 minutes at room temperature (20° C.) whilst being stirred slowly (20 rpm).

2-d. Characterisation of the Coupled Peptide

Method:

The concentration of the coupled peptide was then determined by the Bradford method (Bradford M., Anal. Biochem., 1976; 72: 248-54) as follows: a standard range of from 50 to 1000 µg/mL of KLH was prepared in order to determine the KLH concentration of our sample from the OD at 595 nm. In order to produce this standard range and to carry out this assay, 50 µL of each point of the sample were diluted in 1.5 mL of Coomassie blue (Bio-Rad, #1856210).

Having determined the concentration, PBS was added to the KLH-coupled peptide to bring the concentration of the coupled peptide to 1 mg/mL.

Example 3

Immunisation of Mice and Production of Monoclonal Antibodies 3-a) Immunisation of Mice:

In order to produce monoclonal antibodies, ten mice (Balb/c strain females, 5 weeks old, ref: SIFE055, Charles Rivers, Mass., USA) were immunised using one of the following peptides:

```
Ac-TGCFGRKMDRISTSTAIGCKVL-Cys-CONH2, (SEQ ID NO: 4)
Ac-SGCYGRKMDRISTSTAIGCKVL-CysCONH2, (SEQ ID NO: 5)
``` coupled to KLH in accordance with Example 2 (5 mice for each peptide).

For the first injection, an emulsion of 100 µg of KLH-coupled peptide (at a concentration of 1 mg/ml) diluted to ½ in Freund's complete adjuvant (Sigma, # F-5881) was prepared, and 200 µL of said emulsion (i.e. 100 µg of peptide) were injected subcutaneously into each mouse. At intervals of 20 days, three 200 µL booster shots of an emulsion of KLH-coupled peptide (i.e. 100 µg of peptide) and Freund's incomplete adjuvant (Sigma, #F-5506) were injected subcutaneously, then peritoneally, into each mouse.

20 days after the last booster shot, and after the antibodies obtained had been assessed by the ELISA method (in accordance with Example 4 described below), the mouse with the greatest reaction against BNP(1-32) was retained in order to undergo hyperimmunisation, in accordance with the following protocol:

subcutaneous injection of 200 µL of peptide-KLH at 1 mg/mL diluted to $\frac{1}{20}^{th}$ with PBS
45 minute-wait
subcutaneous injection of 200 µL of peptide-KLH at 1 mg/mL diluted to $\frac{1}{20}^{th}$ with PBS at a site different from the first injection
45 minute-wait
subcutaneous injection of 200 µL of peptide-KLH at 1 mg/mL diluted to $\frac{1}{10}^{th}$ with PBS at a site different from the previous injections
30 minute-wait
intraperitoneal injection of 100 µL of promethazine (2.5% Phenergan, injectable solution, UCB) diluted to 1 mg/mL with PBS
15 minute-wait
intraperitoneal injection of 200 µL of peptide-KLH at 1 mg/mL diluted to $\frac{3}{10}^{ths}$ with PBS at a site different from the previous injections After these immunisations, the mouse S2 immunised with the SEQ ID NO: 4 peptide was found to produce an antiserum which was very reactive towards BNP(1-32) when using the protocol for detecting antibodies described below in Example 4. The lymphocytes from the spleen of said mouse were subsequently subjected to lymphocyte fusion, carried out in accordance with the protocol described below in 3b.

3-b) Production of Monoclonal Antibodies:

Lymphocyte fusion of the spleen cells of the immunised mouse S2 with myeloma SP2 cells (ATCC CRL-1581) was carried out in accordance with Köhler and Milstein's well known protocol (1975) Nature 56:495-497.

The inventors were thus able to produce different hybrid clones. In particular, they obtained a monoclonal antibody, which was given the designation 20G7-15/03/2007 (referred to as "20G7" in the following for convenience). The hybridoma which secretes the 20G7-15/03/2007 (20G7) monoclonal antibody was deposited at the CNCM (French National Collection of Cultures of Microorganisms, Institut Pasteur, 25, rue du Docteur Roux, 75 724 Paris Cedex 15, France) with the registration number CNCM I-3746 on Apr. 13, 2007.

It goes without saying that other protocols for obtaining monoclonal antibodies which are well known to the one skilled in the art may be used.

Example 4

Detection of Anti-BNP(1-32) Antibodies to Assess the Response of Mice During Immunisation 4.1 Materials:
The following reagents were used:
Maxisorp 96-well flat-bottomed microplate (Nunc, Denmark)
PBS (phosphate buffered saline) buffer, pH 7.4, Gibco tablets, ref: 18912-014 (Invitrogen)
BNP(1-32): synthetic peptide (Sigma-Aldrich, USA, #B-5900)
or
proBNP(1-108) (recombinant protein produced in *E. Coli*, HyTest, Finland)
Tween® 20 (Sigma-Aldrich, USA, #P1379)
anti-mouse IgG secondary antibody produced in rabbit and coupled to peroxidase, (Sigma, USA, #A9044)
$H_2O_2$ (0.04% in 0.1 M citrate buffer, pH 4)
OPD (ortho-phenylenediamine, Sigma, USA, #P8412)
sulphuric acid ($H_2SO_4$, 4N)
serums from mice immunised in Example 3

4.2 Method and Principle:

An ELISA test was carried out on a solid support to detect the presence of anti-BNP(1-32) antibodies in a mouse serum sample.

Some of the antigen was immobilised by adsorption in the cavities of a 96-well microplate. After the remaining free sites were saturated and blocked, the immune serums were left to incubate, and the antibodies (<<Ac>>) which may have been present bound to the antigen (<<Ag>>) and formed an Ag-Ac complex. This complex was detected using an immunoconjugate (anti-mouse IgG antibody) coupled to an enzyme, which in this case was HRP (horseradish peroxidase), which transforms a colourless substrate into a coloured product which indicates the presence of the desired antibody. The formation of the final coloured product was quantified by carrying out an optical density reading at 490 nm (OD). According to this method, which is well known to the one skilled in the art, the OD obtained indicates the presence (high OD) or absence (low OD) of antibodies in a tested mouse serum sample. There are a number of variants of this test (antigen capture, competition assay . . . ) which are well known to the one skilled in the art.

1) Immobilisation of the Antigen on the Microplate:

Each antigen, BNP(1-32) or proBNP(1-108), was solubilised in PBS at a final concentration of 0.5 µg/mL and was then immobilised, on the basis of 100 µL per well, on a Maxisorp microplate by being incubated overnight at 4° C. After 3 washes with PBS 0.1% Tween® 20 (PBS-T), the microplate was saturated with a solution (100 µL/well) of 0.1% PBS-T containing 1% milk (semi-skimmed) and was then left to incubate at 37° C. for 1 hour.

2) Immunological Detection of the Antibodies Produced by the Mice:

The microplate was washed three times with 0.1% PBS-T. Each serum from previously immunised mice was subsequently diluted tenfold with 0.1% PBS-T containing 0.1% milk (semi-skimmed), then deposited on the basis of 100 µL per well and left to incubate for two hours at 37° C. The microplate was again washed three times with 0.1% PBS-T, then left to incubate for 1 hour at 37° C. in the presence of the conjugate coupled to peroxidase diluted to a 1/3,000$^{th}$ in 0.1% PBS-T containing 0.1% milk (semi-skimmed) on the basis of 100 μL per well. Finally, the microplate was washed three times with 0.1% PBS-T, then the peroxidase substrate was deposited on the basis of 100 μL per well. The microplate was placed in darkness at room temperature for 20 minutes. The enzymatic reaction was stopped by adding 50 μL of sulphuric acid (H$_2$SO$_4$, 4 N) per well, and the OD at 490 nm was subsequently measured in each well.

By using this method for detecting antibodies, the inventors found that the serum from the mouse S2 (immunised with the SEQ ID NO: 4 peptide) was very reactive with BNP(1-32), and proBNP(1-108). Following the lymphocyte fusion which was subsequently carried out between the lymphocytes from said hyperimmune mouse and the Sp2 myeloma, this method also made it possible to identify a hybridoma which produces an important monoclonal antibody: the 20G7 hybridoma, producing the 20G7 monoclonal antibody.

Example 5

Epitopic Characterisation of the 20G7 Monoclonal Antibody 5.1 Epitopic Characterisation According to the <<Spot>> Technique
5.1.1 Materials:
The equipment and reagents are all listed in C. Granier, S. Villard, D. Laune (*Mapping and Characterization of Epitopes using the SPOT method*. Cells/Cell Biology: A Laboratory Handbook, third edition (Volume 1), chapter 62, editor: Julio Celis, Elsevier, 2005).
5.1.2 Method:
The "SPOT" or "epitope mapping" method was used to characterise the epitope of the 20G7 monoclonal antibody. This method, described by Frank (Tetrahedron, 1992; 48: 9217-32), allows synthesis on a cellulose membrane of a large number of peptides with sequences predetermined on a functionalised support (aminopolyethyleneglycol-cellulose) and testing of their reactivity towards a soluble ligand, which is, in the present case, the 20G7 antibody.
5.1.2.1 Peptide Synthesis
The entire peptide synthesis process (amino acid activation, chemical reaction, etc.) is detailed in Molina et al (Pept Res. 1996, Vol. 9: p 151-5), and in C. Granier, S. Villard, D. Laune (*Mapping and Characterization of Epitopes using the SPOT method*. Cells/Cell Biology: A Laboratory Handbook, third Edition (Volume 1), chapter 62, Editor: Julio Celis, Elsevier, 2005).

The BNP(1-32) sequence was synthesised entirely in the form of overlapping pentadecapeptides (SEQ ID NO: 12 to 20), with an offset of two amino acids:

```
SEQ ID NO: 12    SPKMVQGSGCFGRKM
SEQ ID NO: 13    KMVQGSGCFGRKMDR
SEQ ID NO: 14    VQGSGCFGRKMDRIS
SEQ ID NO: 15    GSGCFGRKMDRISSS
SEQ ID NO: 16    GCFGRKMDRISSSSG
SEQ ID NO: 17    FGRKMDRISSSSGLG
SEQ ID NO: 18    RKMDRISSSSGLGCK
SEQ ID NO: 19    MDRISSSSGLGCKVL
SEQ ID NO: 20    RISSSSGLGCKVLRR
```

The other following peptides were also synthesised:

```
SEQ ID NO: 21    VQGSGCFGR
SEQ ID NO: 22    SPKMVQGSGC
SEQ ID NO: 23    MDRISSSSGLG
SEQ ID NO: 24    RKMDRI
SEQ ID NO: 25    RKMDRISS
```

The BNP(1-32) sequence was also synthesised in the form of overlapping decapeptides (SEQ ID NO: 26 to 48), with an offset of 1 amino acid:

```
SEQ ID NO: 26    SPKMVQGSGC
SEQ ID NO: 27    PKMVQGSGCF
SEQ ID NO: 28    KMVQGSGCFG
SEQ ID NO: 29    MVQGSGCFGR
SEQ ID NO: 30    VQGSGCFGRK
SEQ ID NO: 31    QGSGCFGRKM
SEQ ID NO: 32    GSGCFGRKMD
SEQ ID NO: 33    SGCFGRKMDR
SEQ ID NO: 34    GCFGRKMDRI
SEQ ID NO: 35    CFGRKMDRIS
SEQ ID NO: 36    FGRKMDRISS
SEQ ID NO: 37    GRKMDRISSS
SEQ ID NO: 38    RKMDRISSSS
SEQ ID NO: 39    KMDRISSSSG
SEQ ID NO: 40    MDRISSSSGL
SEQ ID NO: 41    DRISSSSGLG
SEQ ID NO: 42    RISSSSGLGC
SEQ ID NO: 43    ISSSSGLGCK
SEQ ID NO: 44    SSSSGLGCKV
SEQ ID NO: 45    SSSGLGCKVL
SEQ ID NO: 46    SSGLGCKVLR
SEQ ID NO: 47    SGLGCKVLRR
SEQ ID NO: 48    GLGCKVLRRH
```

A selection of heptapeptides with an offset of one amino acid were also synthesised (SEQ ID NO: 49 to 53):

```
SEQ ID NO: 49    GCFGRKM
SEQ ID NO: 50    CFGRKMD
SEQ ID NO: 51    FGRKMDR
```

-continued

SEQ ID NO: 52    GRKMDRI

SEQ ID NO: 53    RKMDRIS 5.1.2.2 Immunological Test

The followed test for immunoreactivity has been described in detail in Laune et al (J. Immunol. Methods, 2002, Vol. 267(1), p 53-70). In short, the principle was as follows. The membrane was rehydrated by three TBS baths (tris-buffered saline, pH 7.0) with a duration of 10 minutes in each case, and was subsequently saturated by being incubated overnight at room temperature, whilst being stirred, in the presence of 15 ml of a 10% saturation buffer ("blocking buffer", Roche) and 5% saccharose in TBS 0.1% Tween® 20 (TBS-T). After the membrane was washed three times for 10 minutes with 0.1% TBS-T, the membrane was left to incubate for 90 minutes at 37° C. whilst being stirred, in the presence of the antibody to be tested (20G7 in this case) and the conjugate coupled to alkaline phosphatase diluted with the saturation buffer. After washing the membrane twice with 0.1% TBS-T, then twice with CBS (citrate buffered saline), each bath lasting 10 minutes, the alkaline phosphatase substrate was added and the membrane was incubated at room temperature for 1 to 30 minutes, depending on the speed at which the signal appeared.

5.1.2.3 Results

In the present case, the BNP(1-32) sequence was synthesised entirely in the form of overlapping pentadecapeptides (SEQ ID NO: 12 to 20), with an offset of two amino acids. As shown in FIG. 1, when the peptides are contacted with the purified 20G7 antibody, only five successive peptides react with the antibody, and the common sequence thereof is $F_{11}GRKMDR_{17}$ (SEQ ID NO: 51) (FIG. 1):

SEQ ID NO: 13
K M V Q G S G C F G R K M D R

SEQ ID NO: 14
V Q G S G C F G R K M D R I S

SEQ ID NO: 15
G S G C F G R K M D R I S S S

SEQ ID NO: 16
G C F G R K M D R I S S S S G

SEQ ID NO: 17
F G R K M D R I S S S S G L G

To ensure that only this pattern is actually involved in the binding of the antibody to BNP(1-32), shorter peptides (decapeptides (SEQ ID NO: 26 to 48) and heptapeptides (SEQ ID NO: 49 to 53) were also synthesised, with an offset of only one amino acid, in order to confirm and validate the epitope. In each experiment, the common peptide sequence identified by 20G7 was $F_{11}GRKMDR_{17}$ (SEQ ID NO: 51) (for decapeptides, SEQ ID NO: 33 to 36, and for heptapeptides, SEQ ID NO: 51).

Figure 2:
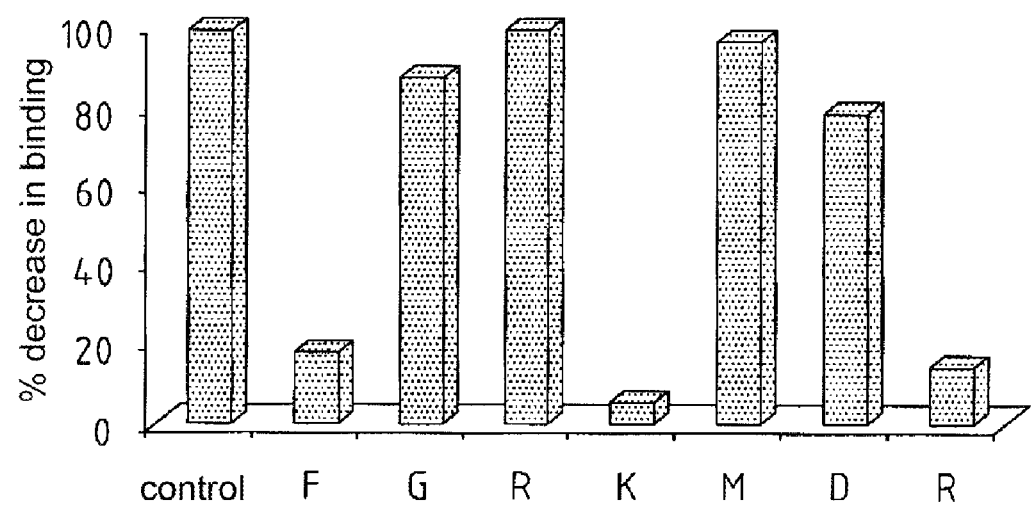
FIG. 2 shows the result of the alascan analysis of the binding of 20G7 antibody to FGRKMDR (SEQ ID NO: 51) epitope (substitution of each residue of the peptide by an alanine), and shows the importance of the F, K, and R residues.

In order to determine which residues are critical and essential for the recognition of the epitope, each residue of the minimal sequence $F_{11}GRKMDR_{17}$ (SEQ ID NO: 51) was substituted successively by an alanine (A) in order to assess the involvement of each individual residue in accordance with the "Alascan" method, which is well known and described (Laune et al, above). As shown in FIG. 2, binding decreased to 82%, 95% and 85% when the $F_{11}$, $K_{14}$ and $R_{17}$ residues were respectively substituted by an alanine, which indicates that these residues are essential.

These amino acids in positions 11, 14 and 17 are essential for the recognition of the epitope by the 20G7 monoclonal antibody. These data are the mean values of a plurality (n=4) of repeat experiments. For this reason, it is therefore clear that the $F_{11}GRKMDR_{17}$ (SEQ ID NO: 51) epitope, comprising the essential $F_{11}$, $K_{14}$ and $R_{17}$ amino acids, according to the invention, is different from that recognised in the patent application WO2006/88700 which discloses another epitope $(R_{13}(K_{14})(M_{15})D_{16}R_{17}I_{18})$ (SEQ ID NO: 24), the important amino acids of which are $R_{13}$, $D_{16}$, $R_{17}$ and $I_{18}$.

In order to achieve a better understanding of the contributory effect of these residues to the binding process of the 20G7 antibody, the $F_{11}$, $K_{14}$ and $R_{17}$ amino acids were substituted by amino acids with closed biochemical properties. For example, $F_{11}$ was substituted by other aromatic amino acids (tryptophan and tyrosine). The fact that the sequence composed of these "homologous" amino acids was recognised in the same way by the 20G7 antibody suggests that it is the aromatic nature of the peptide in position 11 that is essential for the antibody binding. With regard to $K_{14}$ and $R_{17}$, they were both substituted by an arginine and a lysine to study the effect of the lateral chain of the amino acid, and also the presence of a positive charge. It was also found in this case that the substitution was effectively conservative, since binding to 20G7 was retained, thus underlining the importance of the positive charge.

The same does not apply to the 24C5 antibody from HyTest, which has different essential residues.

The VQGSGCFGR, SPKMVQGSGC, MDRISSSSGLG, $R_{13}KMDRI_{18}$ and $R_{13}KMDRISS_{20}$ (SEQ ID NO: 21 to SEQ NO: 25) peptide sequences of human BNP(1-32), which were also synthesised on a membrane, were tested with the 20G7 antibody using the Spot method. Since residues which are essential for the binding of 20G7 were absent, said antibody did not bind to said peptides at all, with the result that 20G7 exhibited a cross reaction of less than 2% with these peptides.

5.2 Characterisation with Soluble Peptides

In a second step, to ensure that the $F_{11}GRKMDR_{17}$ (SEQ ID NO: 51) peptide was really the epitope of the 20G7 antibody, this sequence was synthesized in a soluble form in order to carry out competition assays between this peptide and BNP(1-32). Parallely, in order to confirm the high contribution of the $F_{11}$ residue in the binding to the 20G7 antibody, two other additional peptides (one wherein F was substituted by A, and the other wherein F was simply deleted) were also synthesized in a soluble form. Moreover, similar competition assays were carried out with the 24C5 antibody of Hytest to demonstrate that the importance of this residue is specific of the 20G7 antibody.

1—SEQ ID NO 51: sequence of the native epitope: $F_{11}GRKMDR_{17}$

2—SEQ ID NO 62: mutated sequence of the epitope: $A_{11}GRKMDR_{17}$

3—SEQ ID NO 9: sequence deleted of the $F_{11}$ residue: $G_{12}RKMDR_{17}$ 5.2.1 Materials Maxisorp 96-well flat-bottomed microplate (Nunc, Denmark)

PBS (phosphate buffered saline) buffer, pH 7.4, Gibco tablets, ref: 18912-014 (Invitrogen)

BNP(1-32): synthetic peptide (Sigma-Aldrich, USA, #B-5900)

Tween® 20 (Sigma-Aldrich, USA, #P1379)

monoclonal 20G7 antibody (Bio-Rad)

monoclonal 24C5 antibody (HyTest, Turku, Finland)

anti-mouse IgG secondary antibody produced in rabbit and coupled to peroxidase, (Sigma, USA, #A9044)

$H_2O_2$ (0.04% in 0.1 M citrate buffer, pH 4)

OPD (ortho-phenylenediamine, Sigma, USA, #P8412)

sulphuric acid ($H_2SO_4$, 4N)

5.2.2 Methods

The principle of the immunoassay was the same as the one described in 4.2. Briefly, synthetic BNP(1-32) was diluted in PBS buffer to be directly immobilised on a Maxisorp microplate at 0.5 μg/ml. A standard range from 20 to 10,000 ng/ml of each soluble peptide AA11-AA17 (native, mutated or deleted) was prepared in buffer/serum and mixed to 100 μl of monoclonal antibody solution (20G7 or 24C5 antibody), at a final concentration of 0.5 μg/ml in PBS 0.1% Tween® 20 (PBS-T) containing 0.1% milk (semi-skimmed). The binding of the antibody was then detected by an anti-mouse conjugate labelled with peroxydase. The intensity of the response of the 20G7 antibody was compared to the one of monoclonal 24C5 antibody from HyTest. The percentage of inhibition corresponding to the decrease of the recognition of BNP(1-32) in the presence of the soluble peptide was determined for each soluble peptide, in order to determine 1) that the sequence $F_{11}GRKMDR_{17}$ (SEQ ID NO: 51) effectively represents the 20G7 antibody epitope and 2) that the $F_{11}$ residue was essential for the recognition of BNP(1-32) by 20G7.

5.2.3 Results

Figure 3:
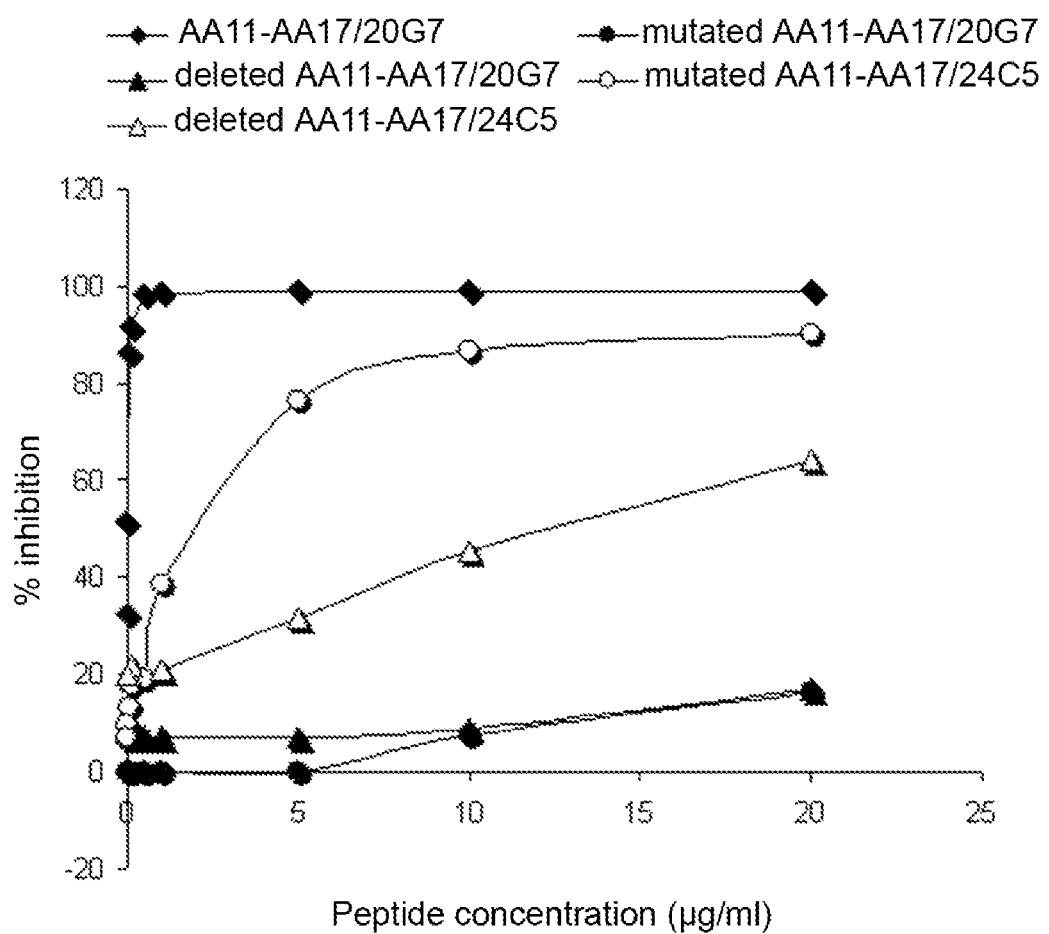
FIG. 3 depicts the inhibition of the binding of antibodies 20G7 and 24C5 to BNP(1-32) in the presence of increasing concentrations of soluble peptide of sequence SEQ ID NO: 51 ("AA11-AA17", diamond), SEQ ID NO: 62 ("mutated AA11-AA17", circle) or SEQ ID NO: 9 ("deleted AA11-AA17", triangle).

FIG. 3 depicts the percentage of inhibition of the binding of the monoclonal antibody (20G7 or 24C5) to BNP(1-32) in the presence of increasing concentrations of soluble peptides (native: SEQ ID NO: 51, mutated: SEQ ID NO: 62, deleted: SEQ ID NO: 9).

It is highly remarkable to note the 20G7 antibody of the present invention behaves distinctly from the 24C5 antibody in the recognition of BNP(1-32) in the presence of the soluble AA11-AA17 peptide mutated (SEQ NO:62) or deleted (SEQ NO:9). Adding soluble peptide mutated ($A_{11}GRKMDR_{17}$ (SEQ ID NO: 62)) or deleted ($G_{12}RKMDR_{17}$) (SEQ ID NO: 9) does not inhibit the recognition of BNP(1-32) by 20G7, whatever the added peptide concentration (up to 20 μg/ml), whereas a total inhibition is observed when the native peptide ($F_{11}GRKMDR_{17}$ corresponding to the sequence SEQ ID NO: 51) is added. This experiment confirms the importance of the $F_{11}$ residue in the binding of the 20G7 antibody to BNP(1-32), on the contrary to the 24C5 antibody.

Example 6

Epitopic Characterisation of Other Anti-BNP(1-32) Monoclonal Antibodies—Comparison with the 20G7 Antibody 6.1. Materials, Methods and Protocols:

The same nitrocellulose membranes and the same conditions of reactivity as those described in Example 5 were used to study these antibodies.

6.2. Results:

The inventors thus obtained a series of following characterized monoclonal antibodies: 20G7, 11A8, 17F10, Mab1, Mab2 and Mab3. As shown in Table 1, the other monoclonal antibodies have the same epitope as the monoclonal 20G7 of the present invention, i.e. FGRKMDR (SEQ ID NO: 51), but have different essential amino acids compared to 20G7.

TABLE 1

Characteristics of the monoclonal antibodies

| Monoclonal antibody | Immunogen | Epitope | Essential residues |
|---|---|---|---|
| 20G7 | SEQ ID NO: 4 | $F_{11}GRKMDR_{17}$ | F, K and R |
| 11A8 | SEQ ID NO: 4 | $F_{11}GRKMDR_{17}$ | F, G, K and R |
| 17F10 | SEQ ID NO: 4 | $F_{11}GRKMDR_{17}$ | F, K, D and R |
| Mab1 | SEQ ID NO: 4 | $F_{11}GRKMDR_{17}$ | F, G, R and K |
| Mab2 | SEQ ID NO: 4 | $F_{11}GRKMDR_{17}$ | F and K |
| Mab3 | SEQ ID NO: 4 | $F_{11}GRKMDR_{17}$ | F, G, R and K |

Figure 4:
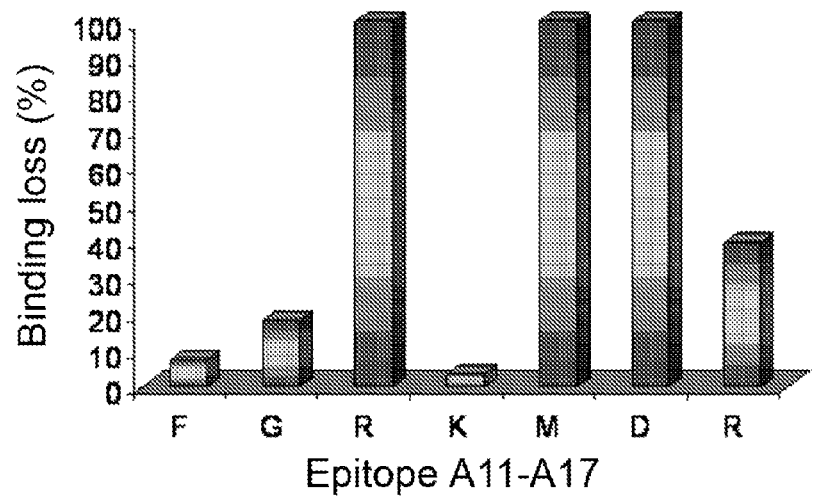
FIG. 4 shows the result of the alascan analysis of the binding of 11A8 antibody to FGRKMDR (SEQ ID NO: 51) epitope (substitution of each residue of the peptide by an alanine) and shows the importance of the F, G, K and R residues.

FIG. 4 shows for example the result of the alascan analysis (successive substitution of each residue of the sequence $F_{11}GRKMDR_{17}$ (SEQ ID NO: 51) by an alanine to assess the individual implication of each residue, method described above in 5.1.2.3) for 11A8 antibody. A substitution of the four residues (F, G, K and R) results in a significant loss of binding of the sequence $F_{11}GRKMDR_{17}$ (SEQ ID NO: 51), demonstrating that they are essential for the binding to BNP(1-32).

Example 7

Characterisation of the Antibody-Antigen Interaction of the Monoclonal Antibodies by Surface Plasmon Resonance Technology 7.1. Materials:

BIAcore® 2000 & 3000 analyser (Pharmacia, Uppsala, Sweden)

BNP(1-32) (synthetic peptide, Sigma, USA, #B-5900)

proBNP(1-108) (recombinant protein produced in *E. Coli*, HyTest, Finland)

anti Fc fragment antibodies (Sigma, USA)

monoclonal antibodies 20G7, 11A8, 17F10 (Bio-Rad, Marnes la Coquette, France)

PBS buffer (phosphate buffered saline), pH 7.4

7.2. Method:

7.2.1. Principle:

The BIAcore® 2000 & 3000 analyser (the principle of which is based on the surface plasmon resonance technology (SPR)), was used to define the kinetics and the affinity of the interaction of the 20G7 monoclonal antibody and other monoclonal antibodies with BNP(1-32) or proBNP(1-108). The inventors followed the manufacturer's instructions.

The surface plasmon resonance SPR technique (BIAcore®, Pharmacia) was described in its entirety in Ferrières et al. (2000, FEBS Letters, 479(3): 99-105). A monoclonal antibody was immobilised on a biosensor or a solid surface by using an anti Fc fragment antibody whilst the soluble antigen (BNP(1-32) or proBNP(1-108)) circulated at increasing concentrations (0.001256 to 0.125 μg/ml) in a constant flow on the surface of the biosensor at room temperature. The angle at which the SPR signal is detected is directly proportional to the refractive index of the medium in which the evanescent wave propagates. The variations in the refractive index are expressed in resonance units (RU, where 1000 resonance units correspond to 1 ng of fixed proteins per $mm^2$ of active area). The quantification of the interaction and the affinity between the antigen and the monoclonal antibody is assessed by calculating the association rate constant (ka) and the dissociation rate constant (kd)

by global data processing using the manufacturer's software BIAevaluation (BIAcore®, Pharmacia, Uppsala, Sweden). The equilibrium dissociation constant (KD=kd/ka) in mol/l reflects the affinity of the BNP(1-32) or proBNP(1-108) antigen for the monoclonal antibody.

7.2.2. Results:

Table 2 shows the characteristics of the interaction between the monoclonal anti-BNP antibodies (including 20G7) and the two recombinant antigens BNP(1-32) and proBNP(1-108).

TABLE 2

Interactions between various monoclonal anti-BNP antibodies and the BNP(1-32) and proBNP(1-108) antigens.

| | ka ($M^{-1}$ $s^{-1}$) | kd ($s^{-1}$) | KA ($M^{-1}$) | KD (M) |
|---|---|---|---|---|
| BNP | | | | |
| 20G7 | 1.40 $10^6$ | 2.38 $10^{-4}$ | 5.90 $10^9$ | 1.70 $10^{-10}$ |
| 11A8 | 8.58 $10^5$ | 2.23 $10^{-3}$ | 3.85 $10^8$ | 2.59 $10^{-9}$ |
| 17F10 | 5.84 $10^5$ | 2.82 $10^{-4}$ | 2.07 $10^9$ | 4.83 $10^{-10}$ |
| ProBNP | | | | |
| 20G7 | 1.02 $10^6$ | 1.74 $10^{-4}$ | 5.90 $10^9$ | 1.69 $10^{-10}$ |
| 11A8 | 7.63 $10^5$ | 1.19 $10^{-3}$ | 6.43 $10^8$ | 1.56 $10^{-9}$ |
| 17F10 | 9.34 $10^5$ | 2.15 $10^{-4}$ | 4.35 $10^9$ | 2.30 $10^{-10}$ |

Table 2 summarises the different characteristics (association rate constant (ka) and dissociation rate constant (kd) values allowing the equilibrium dissociation constant (KD in M) of the interaction between BNP(1-32) or proBNP(1-108) and the monoclonal antibodies to be calculated. These results for the interaction confirm the data obtained with the BNP(1-32) and proBNP(1-108) assays inasmuch as the 20G7 monoclonal antibody exhibits an excellent association constant (ka) and a low dissociation constant (kd), allowing it to be characterised by an excellent affinity constant of $1.70^{-10}$ M, identical for BNP(1-32) and proBNP(1-108) (Table 2).

Examples are also provided for other monoclonal antibodies (11A8 and 17F10), the affinity constants of which are in the nanomolar range ($2 \times 10^{-1\circ}$ to $9.35 \times 10^{-10}$ M, Table 2).

Example 8

BNP(1-32) Assay Using the 20G7 Monoclonal Antibody 8.1. Materials:
Maxisorp 96-well flat-bottomed microplate (Nunc, Denmark)
PBS (phosphate buffered saline) buffer, pH 7.4, Gibco tablets, ref: 18912-014 (Invitrogen)
BNP(1-32) synthetic peptide (Sigma-Aldrich, USA, #B-5900)
proBNP(1-108) (recombinant protein produced in *E. Coli*, HyTest, Finland)
Tween® 20 (Sigma-Aldrich, USA, #P1379)
L21016 rabbit polyclonal antibody obtained by immunising rabbits with an immunogen targeting the 1-10 region of BNP(1-32), its epitope being the sequence $S_1PKMV_5$ (SEQ ID NO: 54) of BNP(1-32)
20G7 monoclonal antibody (Bio-Rad)
24C5 and 26E2 monoclonal antibodies (HyTest, Turku, Finland)
anti-mouse IgG antibody conjugate produced in rabbit and coupled to peroxidase, (Sigma, USA, #A9044)

0.04% $H_2O_2$ in a 0.1 M citrate buffer, pH 4
OPD (ortho-phenylenediamine, Sigma, USA, #P8412)
sulphuric acid ($H_2SO_4$, 4N)

8.2. Method and Principle:

Initially, a standard range of 20 to 10,000 pg/ml of BNP(1-32) was prepared in a buffer/serum from synthetic BNP(1-32).

The assay was based on the sandwich ELISA principle on a microplate, using the L21016 rabbit polyclonal antibody (Bio-Rad) for capture on a solid phase, its epitope being the sequence $S_1PKMV_5$ of BNP(1-32) fixed by passive adsorption by way of 100 µl of 5 µg/ml solution per well.

100 µl of monoclonal antibody solution (20G7, 24C5 or 26E2 antibodies) in solution at a concentration of 0.5 µg/ml in PBS 0.1% Tween® 20 (PBS-T) buffer containing 0.1% milk (semi-skimmed) were used as detection reagents. The intensity of the response of 20G7 was thus compared to that of the 24C5 and 26E2 monoclonal antibodies.

Table 3 summarises the results of the analytical assay of BNP(1-32), expressed in optical density (OD) at 490 nm and obtained by said antibodies in the presence of standard concentrations of BNP(1-32).

TABLE 3

OD values obtained during the analytical assay of BNP(1-32) with different antibodies

| BNP (1-32) (pg/ml) | 20G7 | 24 C5 | 26 E2 |
|---|---|---|---|
| 10,000 | 3.752 | 0.077 | 0.048 |
| 5,000 | 3.056 | 0.068 | 0.041 |
| 2,500 | 1.950 | 0.067 | 0.035 |
| 1,250 | 1.111 | 0.056 | 0.031 |
| 625 | 0.625 | 0.059 | 0.029 |
| 312.5 | 0.404 | 0.063 | 0.027 |
| 156.25 | 0.180 | 0.071 | 0.032 |
| 78 | 0.099 | 0.052 | 0.055 |
| 39 | 0.066 | 0.055 | 0.032 |
| 20 | 0.031 | 0.068 | 0.034 |
| 0 | 0.024 | 0.071 | 0.022 |

It is highly remarkable to note that the two antibodies 24C5 and 26E2 behave quite differently from the 20G7 antibody of the present invention. These results thus confirm that in the latter assay format, 20G7 is much more suitable than the 24C5 and 26E2 antibodies for BNP(1-32) assay.

Figure 5:
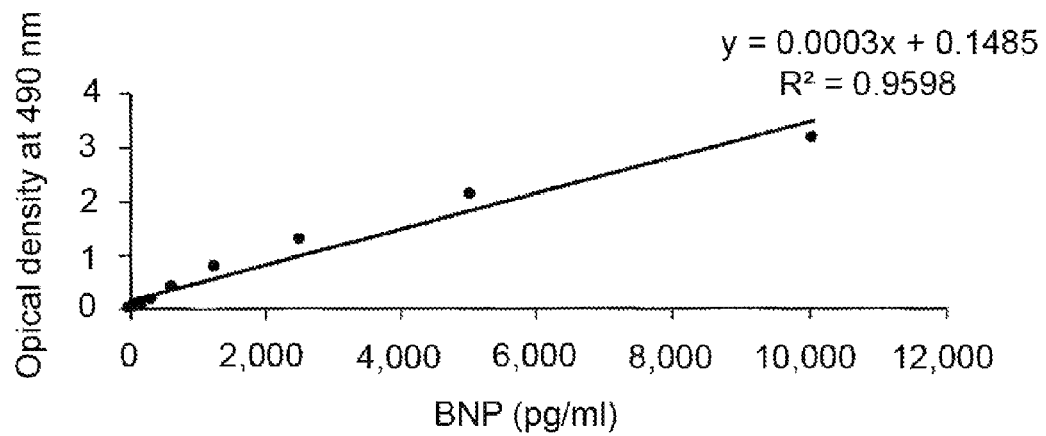
FIG. 5 represents a standard range of BNP(1-32) detected by the 20G7 antibody.

The standard range shown in FIG. 5 and obtained with the 20G7 monoclonal antibody is linear from 20 to 10,000 pg/ml ($r^2=0.96$). The two commercial antibodies 24C5 and 26E2 are not very effective or not at all effective in detecting BNP(1-32), even at high concentrations of the analyte (Table 3).

Example 9

Study of the Complementarity of Monoclonal Antibodies in the Sandwich ELISA 9.1. Materials:
Maxisorp 96-well flat-bottomed microplate (Nunc, Denmark) primed by the L21016 rabbit polyclonal antibody (Bio-Rad) which recognises the sequence $S_1PKMV_5$ (SEQ ID NO: 54) of BNP(1-32)
PBS (phosphate buffered saline) buffer, pH 7.4, Gibco tablets, ref: 18912-014 (Invitrogen)
Tween®20 (Sigma-Aldrich, USA, #P1379)
BNP(1-32) synthetic peptide (Sigma-Aldrich, USA, #B-5900)

proBNP(1-108) (recombinant protein produced in E. Co/i, HyTest, Finland)

20G7 antibody (directed against the epitope $F_{11}GRKMDR_{17}$ (SEQ ID NO: 8) prepared in different concentrations from 0.001 to 1 µg/ml 50B7 monoclonal antibody (HyTest, Finland) which recognises the C-terminal portion of BNP(1-32) at a single concentration of 0.5 µg/ml anti-mouse IgG secondary antibody produced in rabbit and coupled to peroxidase, (Sigma, USA, #A9044)

0.04% $H_2O_2$ (in 0.1 M citrate buffer, pH 4, Sigma, USA)

OPD (ortho-phenylenediamine, Sigma, USA, #P8412)

sulphuric acid ($H_2SO_4$, 4N)

9.2. Method:

9.2.1. Principle:

The assay was based on the sandwich ELISA principle on a microplate, using the L21016 rabbit polyclonal antibody (Bio-Rad) for capture on a solid phase, its epitope being the sequence $S_1PKMV_5$ (SEQ ID NO: 54) of BNP(1-32) fixed by passive adsorption (see Example 8), and a combination of two monoclonal antibodies (the 20G7 monoclonal antibody directed against the epitope $F_{11}GRKMDR_{17}$ (SEQ ID NO: 8) and the 50B7 monoclonal antibody (HyTest, Finland) which targets the C-terminal portion of BNP(1-32)) for detection. However, the 20G7 antibody was used at variable concentrations while the 50B7 monoclonal antibody was used at a constant concentration of 0.5 µg/ml.

The epitopic complementarity of the 20G7 and 50B7 antibodies was studied at variable concentrations of the 20G7 antibody. This format allowed the cooperativity of the two monoclonal antibodies to be assessed in order to improve the BNP(1-32) detection.

9.2.2. Protocol:

100 µl of 5 ng/ml BNP(1-32) solution was added into each microplate well, in which the L21016 polyclonal antibody was adsorbed, and was left to incubate for two hours at 37° C. The microplate was washed three times with 0.1% PBS-T, then 100 µl of a mixture containing the 50B7 antibody and one of the 20G7 antibody dilutions were distributed thereon, and it was left to incubate for 2 hours at 37° C. After three washes with 0.1% PBS-T, the peroxidase—rabbit anti-mouse IgG antibody conjugate (diluted to a ⅓,000th with 0.1% PBS-T and containing 0.1% milk (semi-skimmed), on the basis of 100 µl per well, was left to incubate for 1 hour at 37° C. Finally, after 3 washes with 0.1% PBS-T, the $H_2O_2$+OPD solution was deposited on the basis of 100 µL/well. The microplate was placed in darkness at room temperature for 20 minutes. The enzymatic reaction was stopped by adding 50 µL of sulphuric acid ($H_2SO_4$, 4 N) per well, and the OD at 490 nm was subsequently measured in each well.

9.2.3. Results

Table 4 shows the results of the analytical assay of BNP using the 20G7 and 50B7 monoclonal antibodies, expressed in optical density at 490 nm.

TABLE 4

Cooperativity of the two monoclonal antibodies for detecting BNP(1-32)

| 20G7 range (µg/ml) | Optical Density 490 nm |
|---|---|
| 0.5 | 3.792 |
| 0.1 | 3.753 |
| 0.05 | 3.747 |
| 0.01 | 3.531 |
| 0.005 | 3.272 |
| 0.001 | 1.948 |
| 0 | 1.296 |

It was noted that there is synergism between the two antibodies. In other words, it was noted that the effects of the two antibodies were added: in the absence of 20G7, the signal (OD) was limited to 1.296, and the more 20G7 was added, the more the resulting signal (OD) increased.

By using both the 20G7 monoclonal antibody, which targets the $F_{11}GRKMDR_{17}$ (SEQ ID NO: 8) epitope according to the invention (located in the loop of BNP(1-32)), and the 50B7 monoclonal antibody, which targets the C-terminal region of BNP(1-32), BNP(1-32) detection is significantly improved. This demonstrates the cumulative or cooperative contribution of the two monoclonal antibodies used in detection.

This kind of complementarity may also be envisaged between the 20G7 monoclonal antibody and other antibodies which recognise an epitope located in other positions in the BNP(1-32) sequence (principally in the N-terminal position, C-terminal position). The number of antibodies used may also be greater than two as long as no steric hindrance problems are encountered.

Example 10 proBNP(1-108) Assay Using the 20G7 Monoclonal Antibody 10.1. Materials:

BNP(1-32) synthetic peptide (Sigma-Aldrich, USA, #B-5900)

proBNP(1-108) (recombinant protein produced in *E. Coli*, HyTest, Finland).

Maxisorp 96-well flat-bottomed microplate (Nunc, Denmark) primed with monoclonal antibodies (hinge 76 antibody, for example, from Bio-Rad) which recognises the proBNP(1-108) hinge sequence: epitope $RAPR_{76}S_{77}P$ (SEQ ID NO: 55) (Giuliani et al., Clin. Chem., 52: 6, 1054-1061, 2006)

20G7 monoclonal antibody (Bio-Rad) coupled to peroxidase

24C5 monoclonal antibody (HyTest, Finland) coupled to peroxidase

26E2 monoclonal antibody (HyTest, Finland) coupled to peroxidase

PBS (phosphate buffered saline) buffer, pH 7.4, Gibco tablets, ref: 18912-014 (Invitrogen)

Tween®20 (Sigma-Aldrich, USA, #P1379)

10.2. Method:

10.2.1. Principle of the Analytical Assay of proBNP(1-108):

Initially, a standard range of 20 to 10,000 pg/ml of proBNP(1-108) was prepared in a 0.1% PBS-T buffer from recombinant ProBNP(1-108).

The assay is based on the sandwich ELISA principle on a microplate, using for capture on a solid phase a monoclonal antibody (hinge 76 antibody, for example, from Bio-Rad), and recognising the hinge sequence of proBNP(1-108): epitope $RAPR_{76}S_{77}P$ (SEQ ID NO: 55) fixed by passive adsorption by way of 100 µl of 0.5 µg/ml solution per well.

100 µl of monoclonal antibody solution (20G7, 24C5 or 26E2 antibodies) at a concentration of 0.5 µg/ml and coupled to peroxidase in solution in 0.1% PBS-T buffer (containing 0.1% semi-skimmed milk) were used as detection antibodies.

Besides this technical point, the protocol was identical to that of the ELISA in Example 8. The detection characteristics of 20G7 were thus compared with those of the 24C5 and 26E2 monoclonal antibodies.

Table 5 shows the results of the analytical assay of proBNP(1-108) which are expressed in optical density (OD) and were obtained by using said antibodies in the presence of standard concentrations of proBNP(1-108).

10.3. Results:

TABLE 5

Analytical assay of proBNP(1-108) with different antibodies

| ProBNP(1-108) (pg/ml) | 20 G7 | 24 C5 (Hytest) | 26 E2 (Hytest) |
|---|---|---|---|
| 10,000 | >4 | 0.220 | 0.158 |
| 5,000 | 3.845 | 0.117 | 0.041 |
| 2,500 | 3.272 | 0.069 | 0.031 |
| 1,250 | 1.955 | 0.068 | 0.024 |
| 625 | 0.997 | 0.070 | 0.024 |
| 312.5 | 0.512 | 0.035 | 0.028 |
| 156.25 | 0.264 | 0.055 | 0.027 |
| 78 | 0.126 | 0.056 | 0.033 |
| 39 | 0.092 | 0.056 | 0.028 |
| 20 | 0.069 | 0.052 | 0.028 |
| 0 | 0.045 | 0.044 | 0.024 |

It is highly remarkable to note that the 20G7 antibody of the present invention detects not only BNP(1-32) but also proBNP(1-108). Moreover, in this case too, the two HyTest antibodies behave quite differently from the 20G7 antibody. This confirms the significant benefit of the 20G7 antibody in BNP(1-32) and proBNP(1-108) assays.

Figure 6:
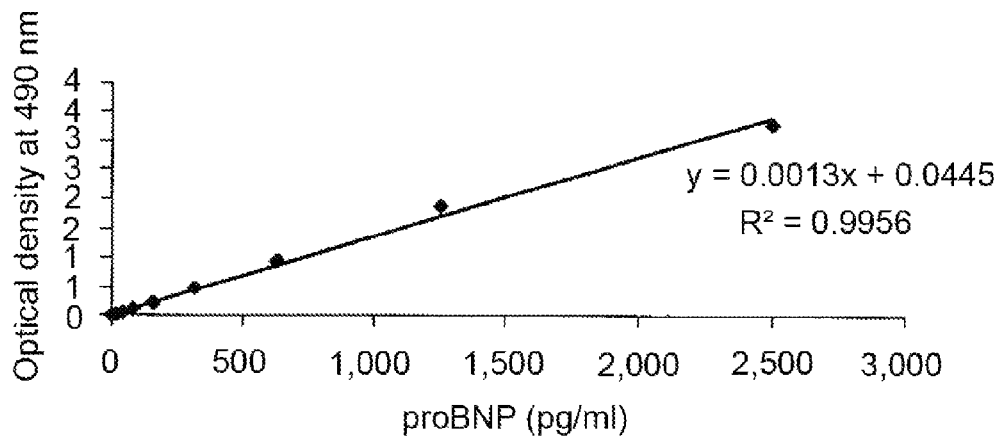
FIG. 6 represents a standard range of recombinant proBNP(1-108) detected by the 20G7 antibody.

FIG. 6 illustrates the linear standard range, obtained with the 20G7 monoclonal antibody, of 20 to 10,000 pg/ml of proBNP ($r^2$=0.99, FIG. 6), whilst the two commercial antibodies from Hytest are not very effective or not effective at all in detecting proBNP(1-108), even at high proBNP(1-108) concentrations (Table 5).

Example 11 proBNP(1-108) and BNP(1-32) Assays Using Other Monoclonal Antibodies Obtained by the Inventors Table 6 shows the results produced, in accordance with the two ELISA protocols from examples 8 and 10, with the 11A8 and 17F10 monoclonal antibodies.

These labelled monoclonal antibodies used in detection are highly capable of detecting BNP(1-32) and proBNP(1-108) when a rabbit polyclonal (L21016) which targets the [1]SPKMV[5] (SEQ ID NO: 54) region or the hinge 76 antibody respectively, are used for capture.

Table 6 shows the results of the analytical assays of proBNP(1-108) and BNP(1-32) which are expressed in optical density and were obtained by said antibodies in the presence of standard concentrations of proBNP(1-108) and BNP(1-32) respectively.

TABLE 6

Analytical assay of proBNP(1-108) and BNP(1-32) with different monoclonal antibodies

| BNP(1-32) or proBNP(1-108) (pg/ml) | proBNP(1-108) | | BNP(1-32) | |
|---|---|---|---|---|
| | 17F10 | 11A8 | 17F10 | 11A8 |
| 10,000 | 3.769 | 3.734 | 3.717 | 3.693 |
| 5000 | 3.808 | 3.779 | 2.712 | 2.534 |
| 2,500 | 3.453 | 3.024 | 1.495 | 1.481 |
| 1,250 | 2.118 | 1.406 | 0.828 | 0.871 |
| 625 | 0.937 | 0.618 | 0.341 | 0.389 |
| 312.5 | 0.489 | 0.259 | 0.172 | 0.211 |
| 156 | 0.242 | 0.130 | 0.095 | 0.123 |
| 78 | 0.139 | 0.088 | 0.070 | 0.114 |
| 39 | 0.125 | 0.087 | 0.059 | 0.097 |
| 20 | 0.100 | 0.078 | 0.059 | 0.071 |
| 0 | 0.076 | 0.063 | 0.059 | 0.068 |

It is highly remarkable to note that the 17F10 and 11A8 antibodies of the present invention detect not only BNP(1-32) but also proBNP(1-108).

Example 12

BNP(1-32) Assay and proBNP(1-108) Assay in Subjects with Congestive Heart Failure and in Normal Subjects 12.1. Samples:

55 EDTA plasmas from subjects with congestive heart failure, who belonged to one of NYHA (New York Heart Association) classes I to III and had signed a voluntary consent form, originating from a commercial source (ProMedex, NY, USA). The studied population is as follows: 10 patients of NYHA class I, 21 patients of NYHA class II and 24 patients of NYHA class III.

48 EDTA plasmas from normal subjects (healthy volunteers, ProMedex, NY, USA).

12.2. Materials and Methods for the BNP(1-32) and the proBNP(1-108) Assays

The materials and methods used were identical to those described above in 8.2 for BNP(1-32), and to those described above in 10.2 for the proBNP(1-108).

Figure 7:
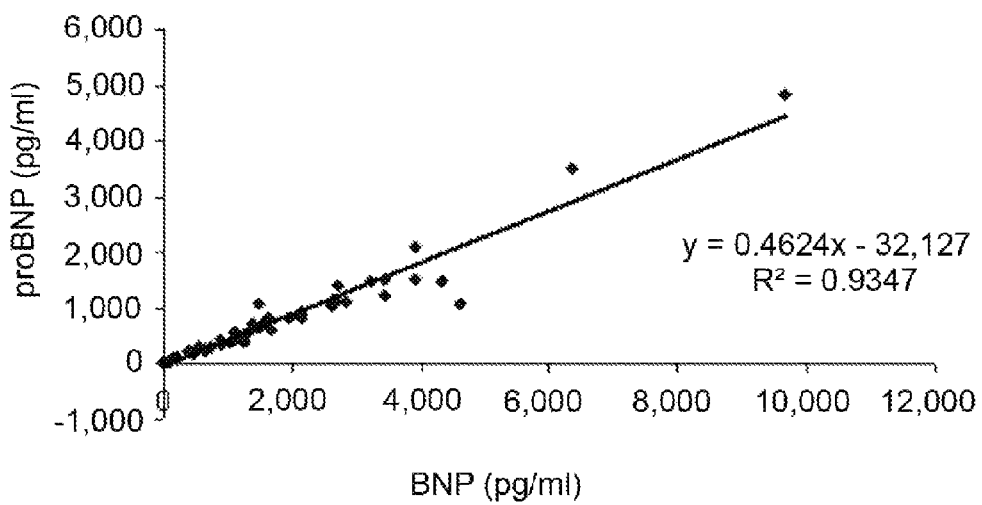
FIG. 7 shows the correlation between the detection of BNP(1-32) and proBNP(1-108) by the 20G7 antibody in patients with congestive heart failure.

12.3 Results 12.3.1. Results of the BNP(1-32) and the proBNP(1-108) Assays in Patients with Congestive Heart Failure The BNP(1-32) values obtained from plasmas from patients with congestive heart failure, by means of the BNP(1-32) assay disclosed in 8.2, were found to correlate with those of the proBNP(1-108) assay according to the invention ($r^2$=0.935, FIG. 7).

Figure 8A:
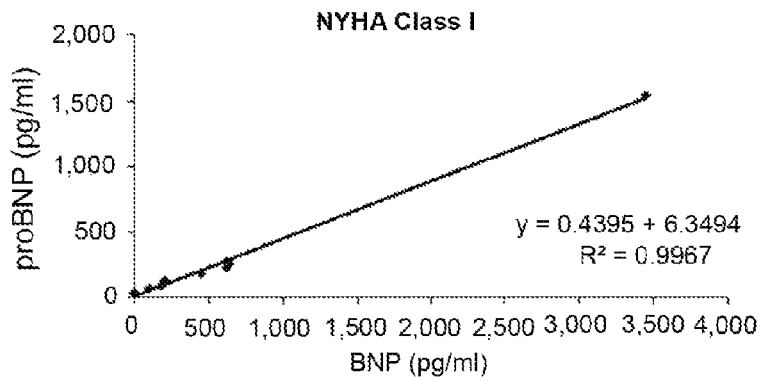
FIG. 8 shows the correlation between the detection of BNP(1-32) and proBNP(1-108) by the 20G7 antibody in samples from subjects with congestive heart failure of NYHA class I (FIG. 8A), NYHA class II (FIG. 8B) and NYHA class III (FIG. 8C).
Figure 8B:
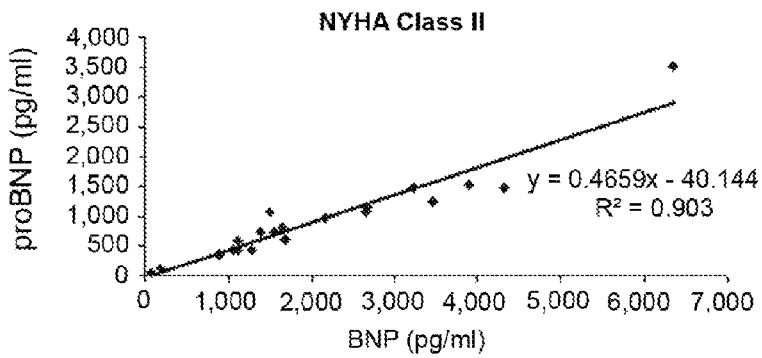
Figure 8C:
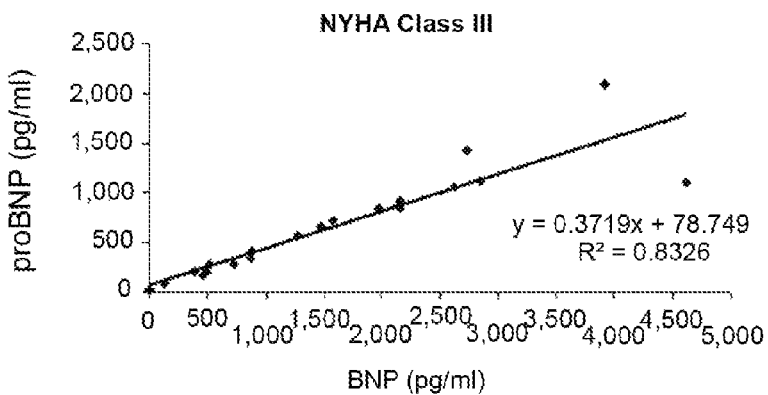

More in detail, correlations are maintained when the patients are studied according to their NYHA class ($r^2$=0.997, $r^2$=0.903, $r^2$=0.832 respectively for the NYHA classes I, II and III, FIG. 8 A, B et C respectively).

Thus, these results with the 20G7 antibody confirm once more the usefulness of the BNP(1-32) or the proBNP(1-108) assay as a marker of congestive heart failure.

These experiments were reproduced with the 24C5 and 26E2 antibodies (HyTest) in a labelled form, but no correlation was observed.

Figure 9:
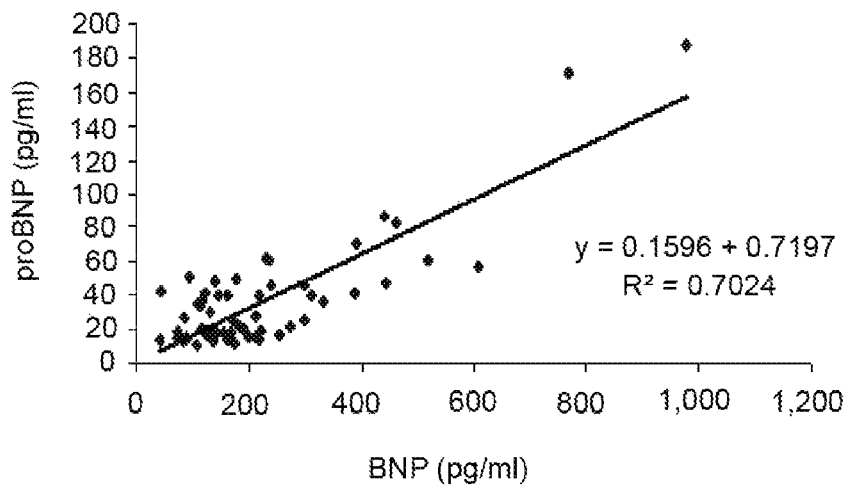
FIG. 9 shows the correlation between the detection of BNP(1-32) and proBNP(1-108) by the 20G7 antibody, in samples from healthy subjects.

12.3.2. Results of the BNP(1-32) and the proBNP(1-108) Assays in Healthy Subjects The proBNP(1-108) values obtained from plasmas from healthy subjects, by means of the proBNP(1-108) assay using the monoclonal hinge 76 antibody in the solid phase and the 20G7 antibody-peroxidase conjugate for detection, were found to be highly correlated ($r^2$=0.702) with those of the BNP(1-32) assay using the 20G7 antibody in detection (FIG. 9).

In conclusion, it is therefore very clear that the 20G7 antibody according to the invention is entirely appropriate for BNP(1-32) and proBNP(1-108) assays in patients suffering from congestive heart failure, by detecting a higher amount of BNP(1-32) and proBNP(1-108) in patients suffering from congestive heart failure than in healthy subjects (Table 7).

TABLE 7

|  | proBNP(1-108) (pg/ml) | BNP(1-32) (pg/ml) |
|---|---|---|
| Healthy subjects | 37 ± 32 | 227 ± 172 |
| NYHA patients | 762 ± 839 | 1716 ± 1754 |

Example 13

Figure 10:
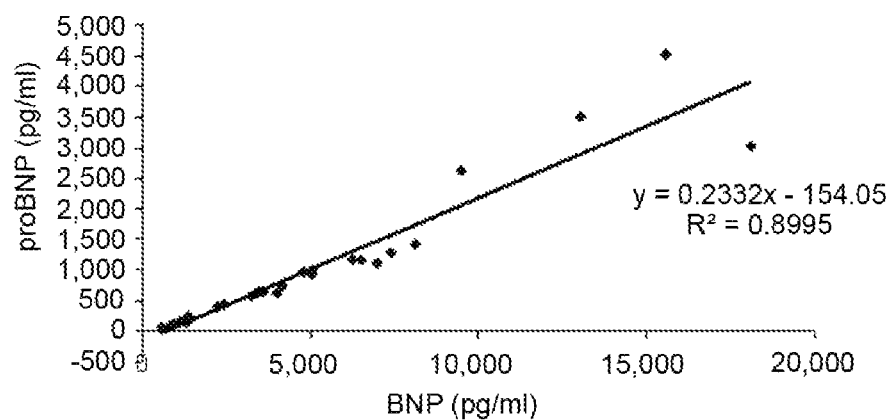
FIG. 10 shows the correlation between the detection of BNP(1-32) and proBNP(1-108) by the 20G7 antibody in samples from subjects with renal failure.

BNP(1-32) and proBNP(1-108) Assays in Patients Suffering from Renal Failure 13.1. Samples:
EDTA plasmas from 33 patients with renal failure who has signed a voluntary consent form, originating from Lapeyronie hospital, Montpellier, France.
13.2. Materials and Methods for the BNP(1-32) and the proBNP(1-108) Assays
The materials and methods used were identical to those described above in 8.2 for BNP(1-32) and in 10.2 for proBNP(1-108).
13.3 Results
The proBNP(1-108) values obtained from plasmas of patients suffering of renal failure, by means of the proBNP(1-108) assay using the hinge 76 antibody in the solid phase and 20G7 antibody-peroxydase conjugate in detection, were found to be strongly correlated ($r^2$=0.899) to those of the BNP(1-32) assay using the 20G7 antibody according to the invention (FIG. 10). The 20G7 antibody according to the invention is highly appropriate for the BNP(1-32) and the proBNP(1-108) assay in patients with renal failure.

Figure 11:
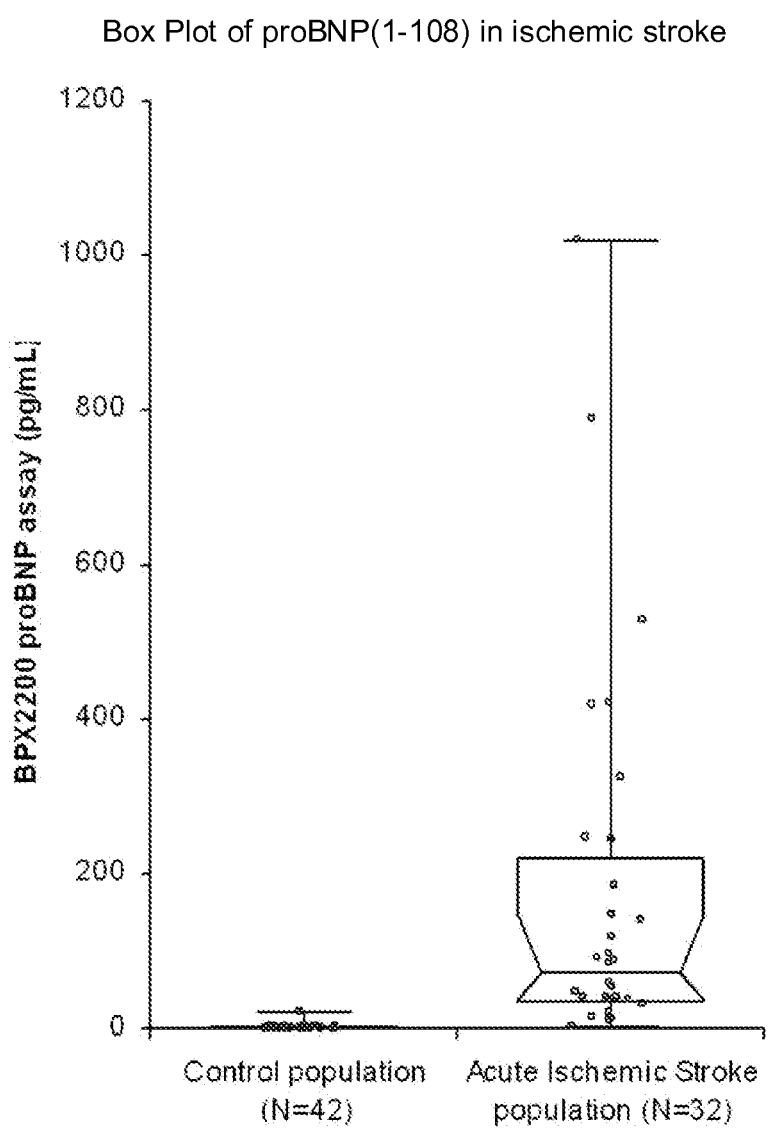
FIG. 11 shows BioPlex™ 2200 proBNP concentrations in ischemic stroke and control citrated plasma samples. Notched box show the minimum, $25^{th}$, $5^{th}$, $75^{th}$ percentiles and the maximum values.

Example 14 proBNP(1-108) Assay in Patients with Ischemic Stroke 14.1. Patients Samples:
32 citrated plasma samples from patients with ischemic stroke admitted to the Emergency Department within 3 hours of the Stroke onset were tested. The stroke severity was assessed by the National Institutes of Health Stroke Scale (NIHSS).
42 citrated plasma samples from apparently healthy blood donor matched by gender and age with the patients from the Stroke population were tested.
All the citrated plasma samples were stored at −80° C. Prior the analysis, the samples were thawed and centrifuged at 3000 g for 15 min at 4° C.
14.2. Material and Method:
All the samples were tested with the BioPlex™ 2200 proBNP assay (Bio-Rad).
14.2.1. Principe of the Technology:
The BioPlex™ 2200 combines multiplex, magnetic bead and flow cytometry technologies to provide multi-analyte detection on a fully automated random access platform. Magnetic particles (8 μm diameter, carboxyl-modified surface) are dyed with two fluorophores (classification dyes, CL1 and CL2) which emit at distinct wavelengths and adsorb significantly at 635 nm. The reporter fluorophore, β-phycoerythrin (PE) was chosen for its high molar extinction coefficient, quantum yield, resistance to photobleaching, lack of self-quenching and stability. The detector simultaneously measures light at three wavelengths: the two classification dyes and the reporter dye.
14.2.2. BioPlex™ 2200 proBNP: Assay Principle
The BioPlex™ 2200 proBNP assay is a two-step sandwich fluorescence immunoassay. In a first step, the Bio-Plex™ 2200 system combines 50 μL of patient sample, magnetic dyed beads coated with the anti-proBNP(1-108) monoclonal antibody (hinge 76 monoclonal antibody recognizing the epitope RAPR$_{76}$S$_{77}$P (SEQ ID NO: 58), Bio-Rad) and assay buffer into a reaction vessel. Then, after 11 minutes of incubation and wash cycles, the anti-human BNP monoclonal antibody 20G7 conjugated to phycoerythrin (PE) is added and incubated for 2 minutes. After removal of excess conjugate, the bead mixture is passed through the detector which identifies the dyed beads and the amount of antigens captured on the beads by the fluorescence of PE. After calibration using a set of six distinct calibrators, the three levels of quality controls and patient samples results are expressed in pg/mL.
Two Quality Control beads are also tested with each sample to enhance the integrity of the overall system.
14.3. Results:
The distributions of the BioPlex™ 2200 proBNP values for the Control and the ischemic stroke populations are shown in Table 8 and FIG. 11. The level of proBNP(1-108) was significantly higher in the ischemic stroke group compared to the control group (Mann-Whitney, p<0.0001). The results demonstrate that the proBNP(1-108) is also a useful plasma biomarker for the early diagnosis of Ischemic stroke.

TABLE 8

BioPlex ™ 2200 proBNP concentrations in ischemic stroke and control citrated plasma samples (minimum, 1$^{st}$ quartile, median, 3$^{rd}$ quartile and maximum values).

| Populations | Minimum (pg/mL) | 1$^{st}$ Quartile (pg/mL) | Median (pg/mL) | 3$^{rd}$ Quartile (pg/mL) | Maximum (pg/mL) |
|---|---|---|---|---|---|
| Control population (N = 42) | 0 | 0 | 1 (IC95%: 0-2) | 2 | 23 |
| Ischemic Stroke population (N = 32) | 2 | 34 | 71 (IC95%: 38-145) | 219 | 1019 |

The inventors clearly demonstrate that the proBNP(1-108) sandwich assay using the monoclonal antibody 20G7 described in this invention can measure proBNP(1-108) concentrations in patients with stroke.

Figure 12:
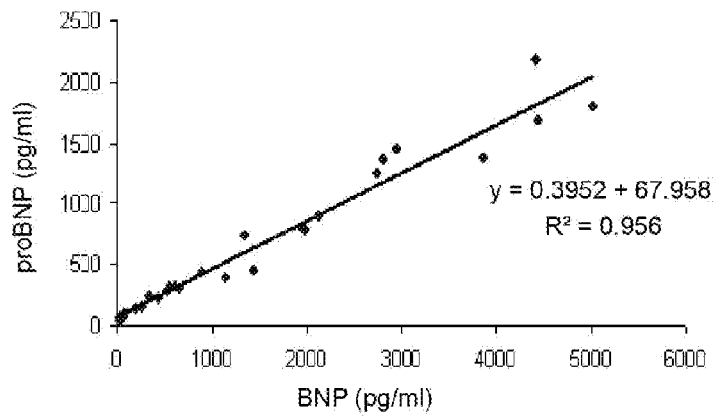
FIG. 12 shows the correlation between the detection of BNP(1-32) and proBNP(1-108) by the 20G7 antibody in samples from subjects with acute coronary syndrome.

Example 15 proBNP(1-108) Assay in Patients Suffering from an Acute Coronary Disorder 15.1. Samples:
EDTA plasmas from 27 patients with an acute coronary disorder (with Troponine I plasma mean values reaching 12.5±6.9 ng/ml) originating from a commercial source (ProMedex, NY, USA)
EDTA plasmas from 48 healthy subjects (healthy volunteers, ProMedex, NY, USA).
15.2. Materials and Methods
The materials and methods used for the BNP(1-32) assay were identical to those described above in 8.2, and for the proBNP(1-108) in 10.2.
15.3 Results
The proBNP(1-108) values obtained from plasmas of patients admitted in emergency and diagnosed for an acute coronary disorder by means of the proBNP(1-108) assay described above, were found to be strongly correlated ($r^2$=0.956) to those obtained with the BNP(1-32) assay using the 20G7 antibody according to the invention (FIG. 12). Levels of BNP(1-32) and proBNP(1-108) of patients with an acute coronary disorder (668±619 and 1,518±1,533 pg/ml for proBNP(1-108) and BNP(1-32) respectively and assayed according to the invention) were higher than those of healthy subjects (37±32 and 227±172 pg/ml for proBNP(1-108) and BNP(1-32) respectively and assayed according to the invention).

It is therefore very clear that the sandwich assay using the 20G7 antibody according to the invention (coupled to peroxidase) allows proBNP(1-108) concentrations, which are proportional to the level of BNP(1-32), to be measured. These results once again prove the usefulness of assaying proBNP(1-108) and BNP(1-32) as markers, in particular as markers of an acute coronary disorder.

Example 16

Assay of proBNP(1-108) in the Glycosylated Form Using the 20G7 Monoclonal Antibody 16.1. Materials:
proBNP(1-108) (recombinant protein produced in *E. coli* for the non-glycosylated form, and from reprogrammed HEK293 cells for the glycosylated form, HyTest, Finland)
Maxisorp™ 96-well flat-bottomed microplate (Nunc, Denmark)
PBS (phosphate buffered saline) buffer, pH 7.4, Gibco tablets, ref: 18912-014 (Invitrogen)
Tween®20 (Sigma-Aldrich, USA, #P1379)
hinge 76 monoclonal antibody which recognises the hinge sequence of proBNP(1-108): epitope RAPR$_{76}$S$_{77}$P (SEQ ID NO: 55) (Giuliani et al., Clin. Chem., 52: 6, 1054-1061, 2006)
20G7 monoclonal antibody (Bio-Rad) coupled to peroxidase
16.2. Method:
16.2.1. Principle of the Analytical Assay of Glycosylated proBNP:

A standard range of 20 to 10,000 pg/ml of glycosylated proBNP(1-108) was prepared in a 0.1% PBS-T buffer. A standard range of 20 to 10,000 pg/ml of non-glycosylated proBNP(1-108) was prepared in the same way in a 0.1% PBS-T buffer.

The assay is based on the sandwich ELISA principle on a microplate, using for capture on a solid phase the monoclonal antibody (hinge 76 antibody, from Bio-Rad), recognising the epitopic sequence RAPR$_{76}$S$_{77}$P (SEQ ID NO: 55) of proBNP(1-108) and fixed by passive adsorption by way of 100 µl of 0.5 µg/ml solution per well.

Figure 13:
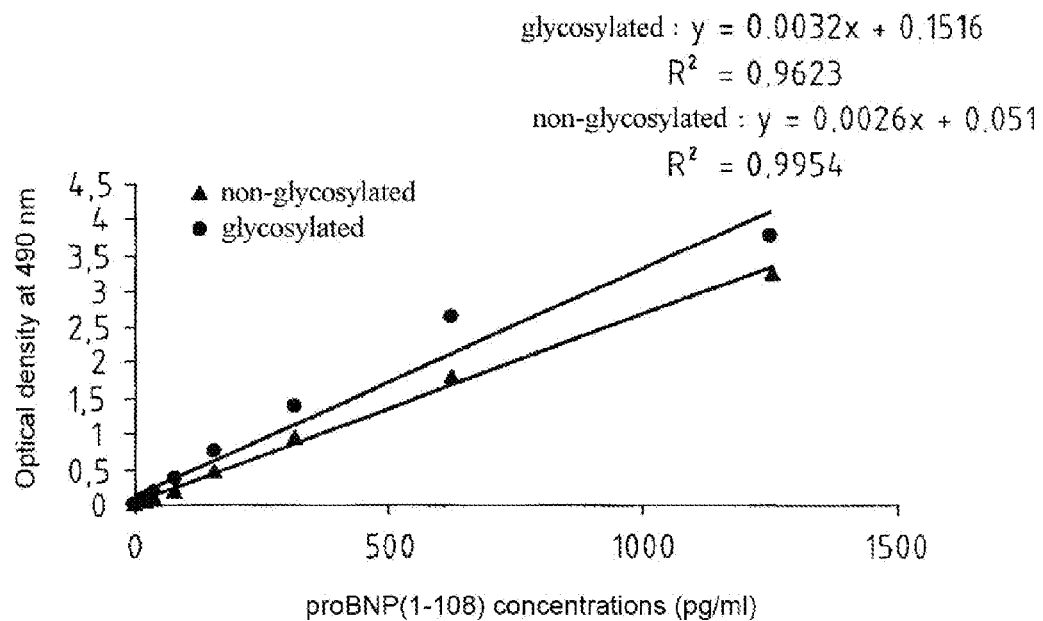
FIG. 13 shows the correlation between the assay of glycosylated proBNP(1-108) and the assay of unglycosylated proBNP(1-108) by immunoassay using the immobilised hinge 76 antibody and in revelation the 20G7 antibody according to the invention.

100 µl of a solution of the 20G7 monoclonal antibody according to the invention coupled to peroxidase at a concentration of 0.5 µg/ml, in solution in 0.1% PBS-T containing 1% milk (semi-skimmed), were used as detection reagents. The rest of the protocol was identical to that of the ELISA in Example 10. The detection characteristics of the 20G7 antibody were thus compared for the two forms of proBNP(1-108)-glycosylated and non-glycosylated.
16.3. Results:
The results shown in Table 9 and FIG. 13 correspond to the glycosylated proBNP(1-108) and non-glycosylated proBNP(1-108) assays by means of immunoassay using the immobilised hinge 76 antibody and the 20G7 antibody for detection.

TABLE 9 optical density values at 490 nm from the assay of each proBNP(1-108) form tested.

| proBNP range (pg/ml) | non-glycosylated proBNP(1-108) | glycosylated proBNP(1-108) |
| --- | --- | --- |
| 10,000 | 4 | 3.833 |
| 5000 | 3.807 | 3.801 |
| 2,500 | 3.829 | 3.023 |
| 1,250 | 3.256 | 1.679 |
| 625 | 1.816 | 0.925 |
| 312.5 | 0.989 | 0.465 |
| 156 | 0.510 | 0.268 |
| 78 | 0.221 | 0.130 |
| 39 | 0.109 | 0.087 |
| 20 | 0.063 | 0.041 |
| 9 | 0.037 | 0.028 |
| 0 | 0.021 | 0.023 |

ProBNP(1-108) can be detected just as well in the non-glycosylated form as in the glycosylated form by using 20G7. The signal/background ratio is slightly greater for non-glycosylated proBNP than for its glycosylated form (signal/background ratios of 3 and 1.8 respectively are obtained at 20 pg/ml).

Example 17

Immunoreactivity of proBNP(1-108) in its Glycosylated Form and Implications for the proBNP(1-108) Assay with the Hinge 76 Antibody 17.1. Materials:
ProteOn XPR36 analyser (surface plasmon resonance SPR technology, Bio-Rad, USA)
proBNP(1-108) (recombinant protein, HyTest, Finland) in the glycosylated and non-glycosylated forms (13 to 200 nM)
anti Fc fragment antibodies (Sigma, USA)
monoclonal hinge 76 antibody (Bio-Rad) which recognises the epitope RAPR$_{76}$S$_{77}$P (SEQ ID NO: 55) and is used at a concentration of 30 µg/ml in 0.1% PBS-T PBS buffer (phosphate buffered saline), pH 7.4

17.2. Method:

17.2.1. Principle:

The ProteOn XPR36 analyser (the principle of which is based on the surface plasmon resonance technology (SPR)), was used to define the kinetics and the affinity of the interaction of the 20G7 monoclonal antibody and with glycosylated and non-glycosylated proBNP(1-108) forms. The inventors followed the manufacturer's instructions. A monoclonal antibody was immobilised on a biosensor (solid surface) by using an anti Fc fragment antibody whilst the glycosylated or non-glycosylated soluble antigen proBNP (1-108) circulated at increasing concentrations (13 to 200 nM) in a constant flow on the surface of the biosensor at room temperature. The angle at which the SPR signal is detected is directly proportional to the refractive index of the medium in which the evanescent wave propagates. The variations in the refractive index are expressed in resonance units (RU, where 1000 resonance units correspond to 1 ng of fixed proteins per $mm^2$ of surface area). The quantification of the interactions and the affinity between the antigen and the monoclonal antibody is assessed by calculating the association rate constant (ka) and the dissociation rate constant (kd) by global data processing using the device software (Bio-Rad). The equilibrium dissociation constant (KD=kd/ka) in mol/l reflects the affinity of the glycosylated or non-glycosylated proBNP(1-108) antigen for the monoclonal antibody.

17.2.2. Results:

Table 10 shows the characteristics of the interaction between the anti-hinge antibody (hinge 76 antibody with the epitope $RAPR_{76}S_{77}P$ (SEQ ID NO: 55) Bio-Rad) and glycosylated and non-glycosylated proBNP(1-108). Although the affinity constant between the anti-hinge antibody and non-glycosylated proBNP(1-108) was greater ($1.73 \cdot 10^{-10}$) than that for glycosylated proBNP(1-108) ($2.35 \cdot 10^{-8}$), the antibody targeting the hinge region of proBNP(1-108) recognised both the glycosylated and non-glycosylated forms with high affinity.

TABLE 10

Reactivity of the hinge 76 antibody towards glycosylated and non-glycosylated proBNP(1-108)

| | Hinge 76 antibody | | |
|---|---|---|---|
| | ka ($M^{-1}s^{-1}$) | kd ($s^{-1}$) | KD = kd/ka M |
| non-glycosylated proBNP(1-108) | $1.12 \cdot 10^6$ | $1.94 \cdot 10^{-4}$ | $1.73 \cdot 10^{-10}$ |
| glycosylated proBNP(1-108) | $1.17 \cdot 10^5$ | $2.72 \cdot 10^{-3}$ | $2.35 \cdot 10^{-8}$ |

Example 18

Biepitopic and Triepitopic Calibrators 18.1. The structure of all of the biepitopic and triepitopic calibrators according to the invention may be linear or branched, provided that the immunoreactivity of the incorporated epitopes is preserved.

The synthesis protocols which may be used to produce these calibrators are those in the field of organic chemistry of peptides well known to the one skilled in the art (in this context, see "Peptide synthesis" in Example 1).

For the epitopes $E_2$ and $E_3$, the linear peptide sequences according to the invention may be selected in a non-limiting manner from the group consisting of the following sequences:

```
SEQ ID NO: 56:      PRSPKMVQG
SEQ ID NO: 57:      APRSPKMV
SEQ ID NO: 58:      SGLGCKLV
SEQ ID NO: 59:      SPKMVQGSG
SEQ ID NO: 60:      YTLRAPRSPKMVG
```

18.2. Examples of Synthesised Epitopes According to the Invention

The inventors synthesised the following calibrators:

18.2.1. Biepitopic Calibrators:

CaliproBNP1: Ac-YTLRAPRSPKMV-Ahx-SFGRKM-DRISS-$CONH_2$ (SEQ ID NO: 66 and SEQ ID NO: 64)

CaliproBNP2: Ac-YTLRAPRSPKMV-Ahx-CFGRKMDRISSSSGLGCK-$CONH_2$ (SEQ ID NO: 66 and SEQ ID NO: 65)

CaliProBNP3: Ac-YTLRAPRSPKMVQG-Ahx-FGRK-MDR-$CONH_2$ (SEQ ID NO: 67 and SEQ ID NO: 51)

These three biepitopic calibrators can be used to calibrate a proBNP(1-108) assay, as described above in 10.2, based on the immobilisation in a solid phase of the monoclonal hinge 76 antibody that recognizes the RAPRSP (SEQ ID NO: 55) (Giuliani et al., supra) and, in detection the monoclonal 20G7 antibody-peroxydase for example.

CaliproBNP4: Ac-FGRKMDR-Ahx-SGLGC*KVLRRH-COOH (SEQ ID NO: 51 and SEQ ID NO: 68)

CaliproBNP4b: Ac-FGRKMDR-Ahx-SGLGC*KVLR-$CONH_2$ (SEQ ID NO: 51 and SEQ ID NO: 69)

These two biepitopic calibrators can be used to calibrate a BNP(1-32) assay, based on the immobilisation in a solid phase of the monoclonal antibody directed the C-terminal portion of BNP(1-32), such as for example monoclonal antibodies 50B7 or 50E1 (HyTest, Finland) and, in detection the monoclonal 20G7 antibody-peroxydase for example.

CaliproBNP5: Ac-SPKMVQGSG-Ahx-FGRKMDR-$CONH_2$ (SEQ ID NO: 59 and SEQ ID NO: 51)

This biepitopic calibrator can be used to calibrate a BNP(1-32) assay, as described above in 8.2, based on the immobilization in a solid phase of the polyclonal antibody L21016 (Bio-Rad) and, in detection the monoclonal 20G7 antibody-peroxydase for example.

In the calibrators sequences described above, the structural formula of the Ahx group is NH—$(CH_2)_5$—CO.

The binding group of formula —NH—$(CH_2)_5$—CO— is derived from a well-known coupling agent, amino-hexanoic acid (AHX), which enables to covalently couple two peptide sequences together.

C*=C(Acm)=Cysteine blocked by an acetamidomethyl (protecting group, well-known from the one skilled in the art).

18.2.2. Triepitopic Calibrators:

CaliproBNP6: Ac-YTLRAPRSPKMV-Ahx-FGRKMDR-Ahx-SGLGC*KVLRRH-COOH (SEQ ID NO: 66 and SEQ ID NO: 51 and SEQ ID NO: 68)

CaliProBNP6b: Ac-YTLRAPRSPKMV-Ahx-FGRKMDR-Ahx-SGLGC*KVLR-$CONH_2$ (SEQ ID NO: 66 and SEQ ID NO: 51 and SEQ ID NO: 69)

These two triepitopic calibrators can be used to calibrate both a proBNP(1-108) and a BNP(1-32) assay, using antibodies such as the monoclonal hinge 76 antibody that recognizes the sequence RAPRSP (SEQ ID NO: 55) (Giuliani et al., supra) and the monoclonal 20G7 antibody of the invention and an antibody with an epitope directed against the C-terminal portion of BNP(1-32) for example.

18.3. Materials and Methods

To depict the usefulness of these calibrators, results of calibration and stabilities are displayed in two different formats, BioPlex™ assay and ELISA assay.

The proBNP(1-108) biepitopes, the CaliproBNP1 and CaliproBNP3 compounds, were tested by means of the BioPlex™ 2200 proBNP assay as described in Example 14.

The BNP(1-32) bioepitope, the CaliproBNP5 compound, was tested by means of the assay described in Example 8.2 and the triepitope, the CaliproBNP6 compound was tested by means of the assay described in Example 10.2.

18.4. Protocole

The different compounds were tested at different concentrations diluted in 0.1 M succinate buffer, pH 7.6, containing 5% BSA, 2 mM CaCl$_2$, 10% antiproteases cocktail (Sigma reference P2714), 0.1% Proclin, 0.095% NaN$_3$ and 0.1% sodium benzoate.

The CaliproBNP1 calibrator was diluted to 1 μg/mL, 0.2 μg/mL, 0.1 μg/mL, and 0.02 μg/mL, the CaliproBNP3 calibrator was diluted to 1.6 μg/mL, 0.8 μg/mL, 0.3 μg/mL, 0.06 μg/mL, the CaliproBNP5 and CaliproBNP6 calibrators were diluted to from 100 ng/ml to 0.01 ng/ml in the same 0.1 M succinate buffer, pH 7.6.

The compounds stability was studied in accelerated condition (room temperature) compared to synthetic BNP(1-32) (Sigma-Aldrich, Etats-Unis, # B-5900) and recombinant proBNP(1-108) (HyTest Ref. 8PRO8) in the following way:

Recombinant proBNP(1-108), synthetic BNP(1-32) and calibrator peptides were diluted in 0.1 M succinate buffer, pH 7.6 described above. Each solution was divided in 10 tubes placed at room temperature (20° C.±5° C.). Then one tube of each solution was freezed at J0, J+7, J+14, J+21. At J+21, the different solutions were thawed and assayed by means of the BioPlex™ 2200 proBNP assay described in Example 14 or of the immunoassays described in Examples 8.2 and 10.2.

In the ELISA assay, a range of proBNP(1-108), BNP(1-32) and CaliproBNP6 from 25 ng/mL to 0.04 ng/mL was tested. For CaliBNP4 and CaliBNP5, the tested range was from 2 ng/mL to 0.004 ng/mL.

In the BioPlex™ 2200 proBNP assay, the stability of two concentrations of proBNP(1-108), 10 ng/mL and 1 ng/mL, of CaliproBNP1, 2 μg/mL and 0.125 μg/mL and CaliproBNP3, 1 μg/mL and 0.3 μg/mL, were analyzed. In ELISA format, three concentrations of proBNP(1-108) and BNP(1-32), 1.56 ng/mL, 0.78 ng/ml and 0.39 ng/mL, and of CaliproBNP5, 62.5 pg/mL, 31 ng/mL and 15.6 ng/mL, were analysed.

Figure 14:
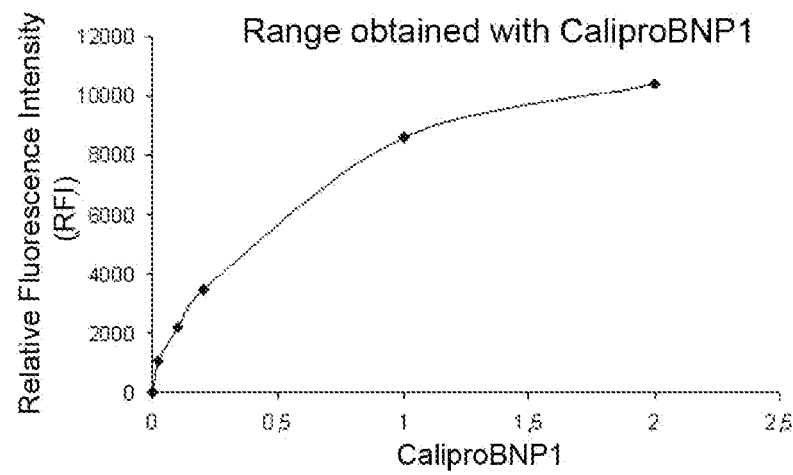
FIGS. 14 and 15 show a standard range of the biepitopic calibrators, CaliproBNP1 and CaliproBNP3, respectively, by using the Bioplex™ 2200 device.
Figure 15:
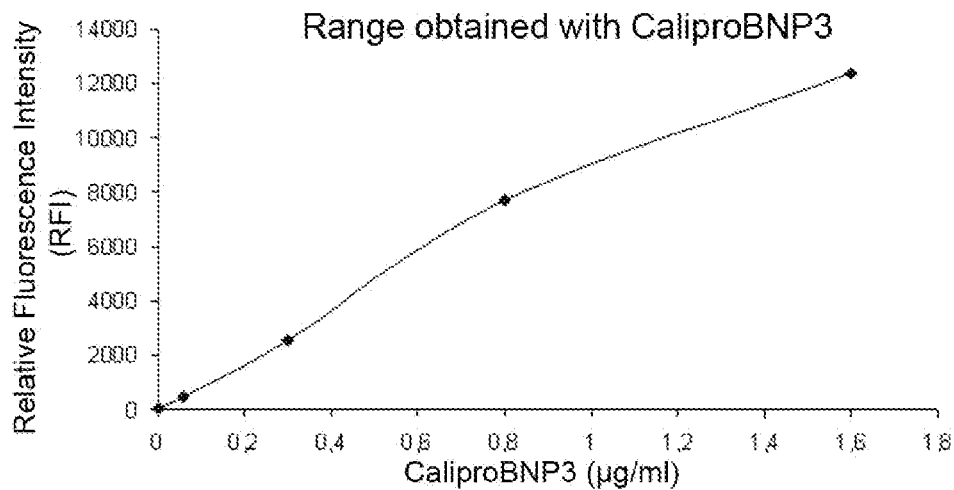

18.5. Results 18.5.1 CaliproBNP1 and CaliproBNP3 Calibrators in the BioPlex™ 2200 proBNP Assay The results of the assay of the CaliproBNP1 and CaliproBNP3 compounds in range of different concentrations are displayed in FIGS. 14 and 15 respectively.

In a BioPlex™ 2200 proBNP assay, the CaliproBNP1 and CaliproBNP3 compounds enable to generate increasing signal with the compound concentration. These compounds are therefore usable as calibrators of the proBNP(1-108) assay, once standardized on the proBNP(1-108) molecule.

The results of the accelerated stability test of the recombinant proBNP(1-108) and the CaliproBNP1 and CaliproBNP3 compounds in range of different concentrations are displayed in Table 11.

TABLE 11

| Compound | Concentration (μg/mL) | Liquid stability* at room temperature** in buffer*** expressed by the ratio "signal at J0 + X/signal at J0" | | |
|---|---|---|---|---|
| | | J0 + 7 | J0 + 14 | J0 + 21 |
| recombinant proBNP(1-108) | 0.001 | 0.79 | 0.65 | 0.51 |
| | 0.01 | 0.85 | 0.72 | 0.69 |
| CaliproBNP1 | 0.125 | 0.93 | 0.92 | 0.95 |
| | 2 | 0.95 | 0.93 | 0.91 |
| CaliproBNP3 | 0.3 | 0.91 | 0.98 | 1.15 |
| | 1 | 0.92 | 1.02 | 1.06 |

*Norme of acceptance of stabilities: to make the stability at day X after J0 accetable, the ratio signal at J0 + X/signal at J0 has to be equal to 1.00 ± 0.2.
**Room temperature: 20° C. ± 5° C.
***0.1 M succinate buffer, pH 7.6, containing 5% BSA, 2 mM CaCl$_2$, 10% antiproteases cocktail (Sigma reference P2714), 0.1% Proclin, 0.095% NaN3 and 0.1%. sodium benzoate.

Biepitopic calibrators CaliproBNP1 and CaliproBNP3 clearly show a higher stability than recombinant proBNP(1-108).

Figure 16:
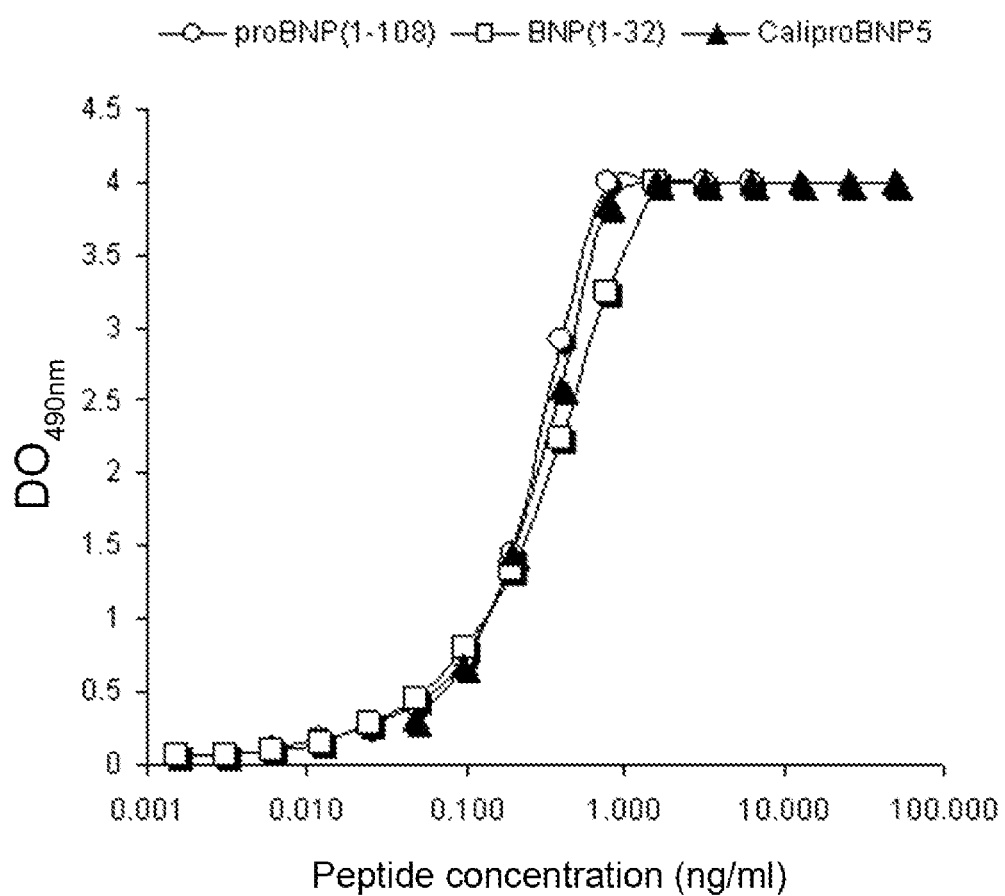
FIG. 16 shows a standard range of the biepitopic calibrator CaliproBNP5, proBNP(1-108) and BNP(1-32) by immunoassay using the immobilised polyclonal antibody L21016 and in revelation the 20G7 antibody according to the invention.
Figure 17:
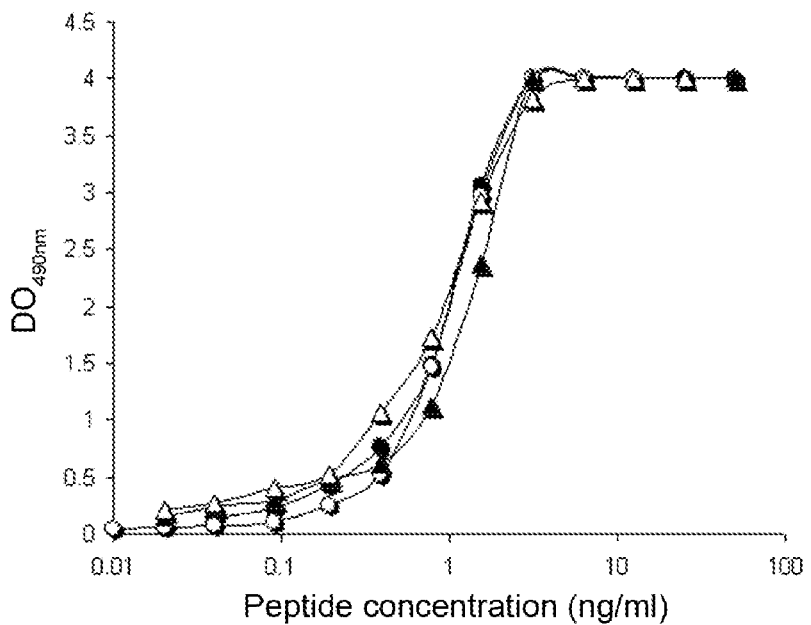
FIG. 17 shows a standard range of the triepitopic calibrator CaliproBNP6 and proBNP(1-108) in two immunoassay formats: one based on the immobilisation of the hinge 76 antibody and in revelation the 20G7 antibody according to the invention (open and close circle), and the second one based on the immobilisation of the hinge 76 antibody and in revelation an antibody directed against an epitope localised in the C-terminal part of the BNP(1-32) (open and close triangle).

18.5.2 CaliproBNP5 and CaliproBNP6 Calibrators in Immunoassays Based on the Use of 20G7 Antibody The results of the test of the CaliproBNP5 and CaliproBNP6 compounds in range of different concentrations are displayed in FIGS. 16 and 17, respectively.

In the BNP(1-32) and the proBNP(1-108) assay, the biepitopic compound CaliproBNP5 and the triepitopic compound CaliproBNP6 enable to generate a signal increasing with the compound concentration. These compounds are therefore usable as calibrators of the proBNP(1-108) and the BNP(1-32) assay.

The results of the accelerated stability assay of recombinant proBNP(1-108), BNP(1-32) and the CaliproBNP5 compound, in range of different concentrations are displayed in Table 12.

TABLE 12

| Compound | Concentration (μg/mL) | Liquid stability* at room temperature** in buffer*** expressed by the ratio "signal at J0 + X/signal at J0" | | |
|---|---|---|---|---|
| | | J0 + 7 | J0 + 14 | J0 + 21 |
| recombinant proBNP(1-108) | 1.56 | 0.58 | 0.5 | 0.45 |
| | 0.78 | 1.08 | 0.82 | 0.88 |
| | 0.39 | 0.71 | 0.66 | 0.79 |
| synthetic BNP(1-32) | 1.56 | 0.71 | 0.7 | 0.55 |
| | 0.78 | 0.69 | 0.65 | 0.53 |
| | 0.39 | 0.81 | 0.7 | 0.53 |
| CaliproBNP5 | 0.0625 | 1.02 | 1.02 | 1.1 |
| | 0.031 | 1.06 | 1.01 | 1.06 |
| | 0.0156 | 1.1 | 1.01 | 1.10 |

*Norme of acceptance of stabilities: to make the stability at day X after J0 accetable, the ratio signal at J0 + X/signal at J0 has to be equal to 1.00 ± 0.2.
**Room temperature: 20° C. ± 5° C.
***0.1 M succinate buffer, pH 7.6, containing 5% BSA, 2 mM CaCl$_2$, 10% antiproteases cocktail (Sigma reference P2714), 0.1% Proclin, 0.095% NaN3 and 0.1%. sodium benzoate.

Once again, the CaliproBNP5 biepitopic calibrator displays a higher stability than recombinant proBNP(1-108) and BNP(1-32).

Summary table of the sequences

| SEQ ID NO: | SEQUENCES |
|---|---|
| 1 | HPLGSPGSASDLETSGLQEQRNHLQGKLSELQVEQTSLEPLQESPRPTGVWKSREVATEGIRGHRKMVLYTLRAPRSPKMVQGSGCFGRKMDRISSSSGLGCKVLRRH |
| 2 | SPKMVQGSGCFGRKMDRISSSSGLGCKVLRRH |
| 3 | HPLGSPGSASDLETSGLQEQRNHLQGKLSELQVEQTSLEPLQESPRPTGVWKSREVATEGIRGHRKMVLYTLRAPR |
| 4 | TGCFGRKMDRISTSTAIGCKVL |
| 5 | SGCYGRKMDRISTSTAIGCKVL |
| 6 | SGCFGRKMDRISSSSGLGCKVL |
| 7 | SGCFGRKMDRIATSTAIGCKVL |
| 8 | FGRKMDR |
| 9 | GRKMDR |
| 10 | FGRKMD |
| 11 | RKMDRI |
| 12 | SPKMVQGSGCFGRKM |
| 13 | KMVQGSGCFGRKMDR |
| 14 | VQGSGCFGRKMDRIS |
| 15 | GSGCFGRKMDRISSS |
| 16 | GCFGRKMDRISSSSG |
| 17 | FGRKMDRISSSSGLG |
| 18 | RKMDRISSSSGLGCK |
| 19 | MDRISSSSGLGCKVL |
| 20 | RISSSSGLGCKVLRR |
| 21 | VQGSCFGR |
| 22 | SPKMVQGSGC |
| 23 | MDRISSSSGLG |
| 24 | RKMDRI |
| 25 | RKMDRISS |
| 26 | SPKMVQGSGC |
| 27 | PKMVQGSGCF |
| 28 | KMVQGSGCFG |
| 29 | MVQGSGCFGR |
| 30 | VQGSGCFGRK |
| 31 | QGSGCFGRKM |
| 32 | GSGCFGRKMD |
| 33 | SGCFGRKMDR |
| 34 | GCFGRKMDRI |
| 35 | CFGRKMDRIS |
| 36 | FGRKMDRISS |
| 37 | GRKMDRISSS |
| 38 | RKMDRISSSS |
| 39 | KMDRISSSSG |
| 40 | MDRISSSSGL |
| 41 | DRISSSSGLG |
| 42 | RISSSSGLGC |
| 43 | ISSSSGLGCK |
| 44 | SSSSGLGCKV |
| 45 | SSSGLGCKVL |
| 46 | SSGLGCKVLR |
| 47 | SGLGCKVLRR |
| 48 | GLGCKVLRRH |
| 49 | GCFGRKM |
| 50 | CFGRKMD |
| 51 | FGRKMDR |
| 52 | GRKMDRI |
| 53 | RKMDRIS |
| 54 | SPKMV |
| 55 | RAPRSP |
| 56 | PRSPKMVQG |
| 57 | APRSPKMV |
| 58 | SGLGCKVL |
| 59 | SPKMVQGSG |
| 60 | YTLRAPRSPKMVG |
| 61 | FGRKMDRISSSS |
| 62 | AGRKMDR |
| 63 | GCFGRKMDRIS |
| 64 | SFGRKMDRISS |
| 65 | CFGRKMDRISSSSGLGCK |
| 66 | YTLRAPRSPKMV |
| 67 | YTLRAPRSPKMVQG |
| 68 | SGLGCKVLRRH |
| 69 | SGLGCKVLR |

The invention claimed is:

1. A method for preparing antibodies directed against human BNP(1-32) or human proBNP(1-108) as well as fragments of human BNP(132) or of human proBNP(1-108) comprising sequence FGRKMDR (SEQ ID NO: 51), comprising the steps of injecting an animal with a polypeptide coupled to an immunogenic carrier protein, wherein the polypeptide is selected from the group consisting of $a_1$-SGCFGRK-MDR-$a_2$ (SEQ ID NO: 33), $a_1$-GCFGRKMDRI-$a_2$, (SEQ ID NO: 34), $a_1$-CFGRKMDRIS-$a_2$ (SEQ ID NO: 35), $a_1$-FGRKMDRISS-$a_2$ (SEQ ID NO: 36), and a₁-FGRKMDR-a₂ (SEQ ID NO: 51), wherein a₁ is H, a thiol group, alcohol group, aminoxy group, primary amine or secondary amine functional group, an amino carboxyl group, a biotinyl group, or an acetyl group, and wherein a₂ is OH, an NH₂ functional group, or an alcoxyl group, and recovering from the animal produced antibodies directed against human BNP(1-32) or human proBNP(1-108) as well as fragments of human BNP(1-32) or of human proBNP(1-108) comprising the sequence FGRKMDR (SEQ ID NO: 51).

2. A hybridoma deposited on Apr. 13, 2007 at the CNCM (Collection Nationale de Cultures de Microorganismes, Institut Pasteur, 25, rue du Docteur Roux, 75 724 Paris Cedex 15, France) under registration number CNCM I-3746.

3. A ligand specifically recognizing an epitope consisting of the sequence FGRKMDR (SEQ ID NO: 51) and not interacting substantially with any of the peptide sequences VQGSGCFGR (SEQ ID NO; 21), SPKMVQGSGC (SEQ ID NO: 22), MDRISSSSGLG (SEQ ID NO: 23), RKMDRI (SEQ ID NO: 24), and RKMDRISS (SEQ ID NO: 25), wherein said ligand is selected from the group consisting of an antibody and a fragment of said antibody which specifically recognizes the epitope, each of the antibody and the fragment of said antibody containing all the Complementary Determining Regions (CDR) of, as arranged in, the monoclonal antibody produced by the hybridoma deposited on Apr. 13, 2007 at the CNCM (Collection Nationale de Cultures de Microorganismes, Institut Pasteur, 25, rue du Docteur Roux, 75 724 Paris Cedex 15, France) under registration number CNCM I-3746.

4. A method for detecting, in a biological sample, human BNP(1-32) or a derivative of human proBNP(1-108) containing sequence FGRKMDR (SEQ ID NO: 51), comprising the steps of
1) contacting the biological sample with at least one ligand specifically recognizing an epitope consisting of the sequence FGRKMDR (SEQ ID NO: 51) and not interacting substantially with any of the peptide sequences VQGSGCFGR (SEQ ID NO: 21), SPKMVQGDGC (SEQ ID NO: 22), MDRISSSSGLG (SEQ ID NO: 23), RKMDRI (SEQ ID NO: 24), and RKMDRISS (SEQ ID NO: 25), wherein said ligand is selected from the group consisting of an antibody and a fragment of said antibody which specifically recognizes the epitope, under conditions allowing antigen-ligand complexes to form, each of the antibody and the fragment of said antibody containing all the Complementary Determining Regions (CDR) of, as arranged in, the monoclonal antibody produced by the hybridoma deposited on Apr. 13, 2007 at the CNCM (Collection Nationale de Cultures de Microorganismes, Institut Pasteur, 25, rue du Docteur Roux, 75 724 Paris Cedex 15, France) under registration Number CNCM I-3746 and
2) detecting any said complexes which may have formed.

5. A multiepitopic calibrator having the following general formula (III):

$$t_1\text{-}E_1\text{-}L_1\text{-}E_2\text{-}[\text{-}L_{k-1}\text{-}E_k]_n\text{-}t_2 \qquad (III)$$

wherein:
n is an integer between 0 and 8;
k is an integer between 3 and n+2 When n>0;
$E_1$, $E_2$, and $E_k$ are different from one another, one representing the peptide sequence FGRKMDR (SEQ ID NO: 51) except that when n is 0, one of $E_1$ and $E_2$ represents the peptide sequence FGRKMDR (SEQ. ID NO: 51), and the others representing a sequence of 3 to 1.5 amino acids comprised in the sequence of human proBNP (1-108);
$t_1$ represents a hydrogen atom, an acetyl group, a peptide sequence of 1 to 10 amino acids, a peptide sequence of 1 to 10 N-α acetylated amino acids, a biotinyl or biocytinyl group, a peptide sequence of 1 to 10 amino acids carrying a biotinyl or biocytinyl radical, or a linear amino alkyl ($C_1$-$C_{10}$) carbonyl chain;
$t_2$ represents a hydroxyl radical, an amino radical, a peptide sequence of 1 to 10 amino acids, a peptide sequence of 1 to 10 amino acids carrying a terminal amino group, or a linear or branched amino alkyl ($C_1$-$C_{10}$) carbonyl chain; and
$L_1$ and $L_k$ represent —NH—(CH₂)₅—CO—.

6. The multiepitopic calibrator according to claim 5 comprising the following general formula (V):

$$t_1\text{-}E_1\text{-}E_2\text{-}t_2 \qquad (V).$$

7. The multiepitopic calibrator according to claim 5, selected from the group consisting of the multiepitopic calibrators defined by the following formulae:

Ac-YTLRAPRSPKMVQG-L₁-FGRKMDR-NH₂
 (SEQ ID NO: 56 and SEQ ID NO: 51);

Ac-FGRKMDR-L₁-SGLGC*KVLRRH-OH(SEQ ID
 NO: 51 and SEQ ID NO: 68);

Ac-FGRKMDR-L₁-SGLGC*KVLR-NH₂(SEQ ID
 NO: 51 and SEQ ID NO: 69);

Ac-SPKMVQGSG-L₁-FGRKMDR-NH₂(SEQ ID
 NO: 59 and SEQ ID NO: 51);

Ac-YTLRAPRSPKMV-L₁-FGRKMDR-L₂-
 SGLGC*KVLRRH-OH(SEQ ID NO: 66 and
 SEQ ID NO: 51 and SEQ ID NO: 68); and Ac-YTLRAPRSPKMV-L₁-FGRKMDR-L₂-
 SGLGC*KVLR-NH(SEQ ID NO: 66 and SEQ
 ID NO: 51 and SEQ ID NO: 69);

wherein Ac represents an acetyl group and C* represents an acetamidomethyl-blocked cysteine.

8. A kit for detecting human BNP(1-32) or human proBNP(1-108) as well as fragments of human BNP(1-32) or of human proBNP(1-108) comprising sequence FGRKMDR (SEQ ID NO: 51), comprising
(a) a ligand specifically recognizing an epitope consisting of the sequence FGRKMDR (SEQ ID NO: 51) and not interacting substantially with any of the peptide sequences VQGSGCFGR (SEQ ID NO:21), SPKMVQGSGC (SEQ ID NO: 22), MDRISSSSGLG (SEQ ID NO: 23), RKMDRI (SEQ ID NO: 24), and RKMDRISS (SEQ ID NO:25), wherein said ligand is selected from the group consisting of an antibody and a fragment of said antibody which specifically recognizes the epitope, each of the antibody and the fragment of said antibody containing all the Complementary Determining Regions (CDR) of, as arranged in, the monoclonal antibody produced by the hybridoma deposited on Apr. 13, 2007 as the CNCM (Collection Nationale de Cultures do Microorganismes, Institut Pasteur, 25, rue du Docteur Roux, 75 724 Paris Cedex 15, France) under registration number CNCM I-3746, and (b) a multiepitopic calibrator having the following general formula (III):

$$t_1\text{-}E_1\text{-}E_2[\text{-}L_{k-1}\text{-}E_k]_n\text{-}t_2 \quad \text{(III)}$$

wherein:
- n is an integer between 0 and 8;
- k is an integer between 3 and n+2 when n>0;
- $E_1$, $E_2$, and $E_k$ are different from one another, one representing the peptide sequence FGRKMDR (SEQ ID NO: 51) except that when n is 0, one of $E_1$ and $E_2$ represents the peptide sequence FGRKMDR (SEQ ID NO: 51), and the others representing a sequence of 3 to 15 amino acids comprised in the sequence of human proBNP(1-108);
- $t_1$ represents a hydrogen atom, an acetyl group, a peptide sequence of 1 to 10 amino acids, a peptide sequence of 1 to 10 N-α acetylated amino acids, a biotinyl or biocytinyl group, a peptide sequence of 1 to 10 amino acids carrying a biotinyl or biocytinyl radical, or a linear amino alkyl ($C_1$-$C_{10}$) carbonyl chain;
- $t_2$ represents a hydroxyl, radical, an amino radical, a peptide sequence of 1 to 10 amino acids, a peptide sequence of 1 to 10 amino acids carrying a terminal amino group, or a linear or branched amino alkyl ($C_1$-$C_{10}$) carbonyl chain; and
- $L_1$ and $L_k$ represent —NH—$(CH_2)_5$—CO—.

\* \* \* \* \*

SEQUENCE LISTING

<160> NUMBER OF SEQ ID NOS: 69

<210> SEQ ID NO 1
<211> LENGTH: 108
<212> TYPE: PRT
<213> ORGANISM: Homo sapiens

<400> SEQUENCE: 1

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg Ser Pro Lys Met
65                  70                  75                  80

Val Gln Gly Ser Gly Cys Phe Gly Arg Lys Met Asp Arg Ile Ser Ser
                85                  90                  95

Ser Ser Gly Leu Gly Cys Lys Val Leu Arg Arg His
            100                 105

<210> SEQ ID NO 2
<211> LENGTH: 32
<212> TYPE: PRT
<213> ORGANISM: Homo sapiens

<400> SEQUENCE: 2

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 3
<211> LENGTH: 76
<212> TYPE: PRT
<213> ORGANISM: Homo sapiens

<400> SEQUENCE: 3

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg
65                  70                  75

<210> SEQ ID NO 4
<211> LENGTH: 22
<212> TYPE: PRT
<213> ORGANISM: Artificial sequence
<220> FEATURE:
<223> OTHER INFORMATION: proBNP derived sequence

<400> SEQUENCE: 4

```
Thr Gly Cys Phe Gly Arg Lys Met Asp Arg Ile Ser Thr Ser Thr Ala
1               5                   10                  15

Ile Gly Cys Lys Val Leu
            20

<210> SEQ ID NO 5
<211> LENGTH: 22
<212> TYPE: PRT
<213> ORGANISM: Artificial sequence
<220> FEATURE:
<223> OTHER INFORMATION: proBNP derived sequence

<400> SEQUENCE: 5

Ser Gly Cys Tyr Gly Arg Lys Met Asp Arg Ile Ser Thr Ser Thr Ala
1               5                   10                  15

Ile Gly Cys Lys Val Leu
            20

<210> SEQ ID NO 6
<211> LENGTH: 22
<212> TYPE: PRT
<213> ORGANISM: Artificial sequence
<220> FEATURE:
<223> OTHER INFORMATION: proBNP derived sequence

<400> SEQUENCE: 6

Ser Gly Cys Phe Gly Arg Lys Met Asp Arg Ile Ser Ser Ser Ser Gly
1               5                   10                  15

Leu Gly Cys Lys Val Leu
            20

<210> SEQ ID NO 7
<211> LENGTH: 22
<212> TYPE: PRT
<213> ORGANISM: Artificial sequence
<220> FEATURE:
<223> OTHER INFORMATION: proBNP derived sequence

<400> SEQUENCE: 7

Ser Gly Cys Phe Gly Arg Lys Met Asp Arg Ile Ala Thr Ser Thr Ala
1               5                   10                  15

Ile Gly Cys Lys Val Leu
            20

<210> SEQ ID NO 8
<211> LENGTH: 7
<212> TYPE: PRT
<213> ORGANISM: Artificial sequence
<220> FEATURE:
<223> OTHER INFORMATION: proBNP derived sequence

<400> SEQUENCE: 8

Phe Gly Arg Lys Met Asp Arg
1               5

<210> SEQ ID NO 9
<211> LENGTH: 6
<212> TYPE: PRT
<213> ORGANISM: Artificial sequence
<220> FEATURE:
<223> OTHER INFORMATION: proBNP derived sequence

<400> SEQUENCE: 9

Gly Arg Lys Met Asp Arg
1               5
```

<210> SEQ ID NO 10
<211> LENGTH: 6
<212> TYPE: PRT
<213> ORGANISM: Artificial sequence
<220> FEATURE:
<223> OTHER INFORMATION: proBNP derived sequence

<400> SEQUENCE: 10

Phe Gly Arg Lys Met Asp
1               5

<210> SEQ ID NO 11
<211> LENGTH: 5
<212> TYPE: PRT
<213> ORGANISM: Artificial sequence
<220> FEATURE:
<223> OTHER INFORMATION: proBNP derived sequence

<400> SEQUENCE: 11

Arg Lys Met Asp Arg
1               5

<210> SEQ ID NO 12
<211> LENGTH: 15
<212> TYPE: PRT
<213> ORGANISM: Artificial sequence
<220> FEATURE:
<223> OTHER INFORMATION: proBNP derived sequence

<400> SEQUENCE: 12

Ser Pro Lys Met Val Gln Gly Ser Gly Cys Phe Gly Arg Lys Met
1               5                   10                  15

<210> SEQ ID NO 13
<211> LENGTH: 15
<212> TYPE: PRT
<213> ORGANISM: Artificial sequence
<220> FEATURE:
<223> OTHER INFORMATION: proBNP derived sequence

<400> SEQUENCE: 13

Lys Met Val Gln Gly Ser Gly Cys Phe Gly Arg Lys Met Asp Arg
1               5                   10                  15

<210> SEQ ID NO 14
<211> LENGTH: 15
<212> TYPE: PRT
<213> ORGANISM: Artificial sequence
<220> FEATURE:
<223> OTHER INFORMATION: proBNP derived sequence

<400> SEQUENCE: 14

Val Gln Gly Ser Gly Cys Phe Gly Arg Lys Met Asp Arg Ile Ser
1               5                   10                  15

<210> SEQ ID NO 15
<211> LENGTH: 15
<212> TYPE: PRT
<213> ORGANISM: Artificial sequence
<220> FEATURE:
<223> OTHER INFORMATION: proBNP derived sequence

<400> SEQUENCE: 15

Gly Ser Gly Cys Phe Gly Arg Lys Met Asp Arg Ile Ser Ser Ser
1               5                   10                  15

<210> SEQ ID NO 16
<211> LENGTH: 15
<212> TYPE: PRT
<213> ORGANISM: Artificial sequence
<220> FEATURE:
<223> OTHER INFORMATION: proBNP derived sequence

<400> SEQUENCE: 16

Gly Cys Phe Gly Arg Lys Met Asp Arg Ile Ser Ser Ser Ser Gly
1               5                   10                  15

<210> SEQ ID NO 17
<211> LENGTH: 15
<212> TYPE: PRT
<213> ORGANISM: Artificial sequence
<220> FEATURE:
<223> OTHER INFORMATION: proBNP derived sequence

<400> SEQUENCE: 17

Phe Gly Arg Lys Met Asp Arg Ile Ser Ser Ser Ser Gly Leu Gly
1               5                   10                  15

<210> SEQ ID NO 18
<211> LENGTH: 15
<212> TYPE: PRT
<213> ORGANISM: Artificial sequence
<220> FEATURE:
<223> OTHER INFORMATION: proBNP derived sequence

<400> SEQUENCE: 18

Arg Lys Met Asp Arg Ile Ser Ser Ser Ser Gly Leu Gly Cys Lys
1               5                   10                  15

<210> SEQ ID NO 19
<211> LENGTH: 15
<212> TYPE: PRT
<213> ORGANISM: Artificial sequence
<220> FEATURE:
<223> OTHER INFORMATION: proBNP derived sequence

<400> SEQUENCE: 19

Met Asp Arg Ile Ser Ser Ser Ser Gly Leu Gly Cys Lys Val Leu
1               5                   10                  15

<210> SEQ ID NO 20
<211> LENGTH: 15
<212> TYPE: PRT
<213> ORGANISM: Artificial sequence
<220> FEATURE:
<223> OTHER INFORMATION: proBNP derived sequence

<400> SEQUENCE: 20

Arg Ile Ser Ser Ser Ser Gly Leu Gly Cys Lys Val Leu Arg Arg
1               5                   10                  15

<210> SEQ ID NO 21
<211> LENGTH: 9
<212> TYPE: PRT
<213> ORGANISM: Artificial sequence
<220> FEATURE:
<223> OTHER INFORMATION: proBNP derived sequence

<400> SEQUENCE: 21

Val Gln Gly Ser Gly Cys Phe Gly Arg
1               5

<210> SEQ ID NO 22
<211> LENGTH: 10
<212> TYPE: PRT
<213> ORGANISM: Artificial sequence
<220> FEATURE:
<223> OTHER INFORMATION: proBNP derived sequence

<400> SEQUENCE: 22

Ser Pro Lys Met Val Gln Gly Ser Gly Cys
1               5                   10

<210> SEQ ID NO 23
<211> LENGTH: 11
<212> TYPE: PRT
<213> ORGANISM: Artificial sequence
<220> FEATURE:
<223> OTHER INFORMATION: proBNP derived sequence

<400> SEQUENCE: 23

Met Asp Arg Ile Ser Ser Ser Ser Gly Leu Gly
1               5                   10

<210> SEQ ID NO 24
<211> LENGTH: 6
<212> TYPE: PRT
<213> ORGANISM: Artificial sequence
<220> FEATURE:
<223> OTHER INFORMATION: proBNP derived sequence

<400> SEQUENCE: 24

Arg Lys Met Asp Arg Ile
1               5

<210> SEQ ID NO 25
<211> LENGTH: 8
<212> TYPE: PRT
<213> ORGANISM: Artificial sequence
<220> FEATURE:
<223> OTHER INFORMATION: proBNP derived sequence

<400> SEQUENCE: 25

Arg Lys Met Asp Arg Ile Ser Ser
1               5

<210> SEQ ID NO 26
<211> LENGTH: 10
<212> TYPE: PRT
<213> ORGANISM: Artificial sequence
<220> FEATURE:
<223> OTHER INFORMATION: proBNP derived sequence

<400> SEQUENCE: 26

Ser Pro Lys Met Val Gln Gly Ser Gly Cys
1               5                   10

<210> SEQ ID NO 27
<211> LENGTH: 10
<212> TYPE: PRT
<213> ORGANISM: Artificial sequence
<220> FEATURE:
<223> OTHER INFORMATION: proBNP derived sequence

<400> SEQUENCE: 27

Pro Lys Met Val Gln Gly Ser Gly Cys Phe
1               5                   10

<210> SEQ ID NO 28

```
<211> LENGTH: 10
<212> TYPE: PRT
<213> ORGANISM: Artificial sequence
<220> FEATURE:
<223> OTHER INFORMATION: proBNP derived sequence

<400> SEQUENCE: 28

Lys Met Val Gln Gly Ser Gly Cys Phe Gly
1               5                   10

<210> SEQ ID NO 29
<211> LENGTH: 10
<212> TYPE: PRT
<213> ORGANISM: Artificial sequence
<220> FEATURE:
<223> OTHER INFORMATION: proBNP derived sequence

<400> SEQUENCE: 29

Met Val Gln Gly Ser Gly Cys Phe Gly Arg
1               5                   10

<210> SEQ ID NO 30
<211> LENGTH: 10
<212> TYPE: PRT
<213> ORGANISM: Artificial sequence
<220> FEATURE:
<223> OTHER INFORMATION: proBNP derived sequence

<400> SEQUENCE: 30

Val Gln Gly Ser Gly Cys Phe Gly Arg Lys
1               5                   10

<210> SEQ ID NO 31
<211> LENGTH: 10
<212> TYPE: PRT
<213> ORGANISM: Artificial sequence
<220> FEATURE:
<223> OTHER INFORMATION: proBNP derived sequence

<400> SEQUENCE: 31

Gln Gly Ser Gly Cys Phe Gly Arg Lys Met
1               5                   10

<210> SEQ ID NO 32
<211> LENGTH: 10
<212> TYPE: PRT
<213> ORGANISM: Artificial sequence
<220> FEATURE:
<223> OTHER INFORMATION: proBNP derived sequence

<400> SEQUENCE: 32

Gly Ser Gly Cys Phe Gly Arg Lys Met Asp
1               5                   10

<210> SEQ ID NO 33
<211> LENGTH: 10
<212> TYPE: PRT
<213> ORGANISM: Artificial sequence
<220> FEATURE:
<223> OTHER INFORMATION: proBNP derived sequence

<400> SEQUENCE: 33

Ser Gly Cys Phe Gly Arg Lys Met Asp Arg
1               5                   10

<210> SEQ ID NO 34
<211> LENGTH: 10
```

```
<212> TYPE: PRT
<213> ORGANISM: Artificial sequence
<220> FEATURE:
<223> OTHER INFORMATION: proBNP derived sequence

<400> SEQUENCE: 34

Gly Cys Phe Gly Arg Lys Met Asp Arg Ile
1               5                   10

<210> SEQ ID NO 35
<211> LENGTH: 10
<212> TYPE: PRT
<213> ORGANISM: Artificial sequence
<220> FEATURE:
<223> OTHER INFORMATION: proBNP derived sequence

<400> SEQUENCE: 35

Cys Phe Gly Arg Lys Met Asp Arg Ile Ser
1               5                   10

<210> SEQ ID NO 36
<211> LENGTH: 10
<212> TYPE: PRT
<213> ORGANISM: Artificial sequence
<220> FEATURE:
<223> OTHER INFORMATION: proBNP derived sequence

<400> SEQUENCE: 36

Phe Gly Arg Lys Met Asp Arg Ile Ser Ser
1               5                   10

<210> SEQ ID NO 37
<211> LENGTH: 10
<212> TYPE: PRT
<213> ORGANISM: Artificial sequence
<220> FEATURE:
<223> OTHER INFORMATION: proBNP derived sequence

<400> SEQUENCE: 37

Gly Arg Lys Met Asp Arg Ile Ser Ser Ser
1               5                   10

<210> SEQ ID NO 38
<211> LENGTH: 10
<212> TYPE: PRT
<213> ORGANISM: Artificial sequence
<220> FEATURE:
<223> OTHER INFORMATION: proBNP derived sequence

<400> SEQUENCE: 38

Arg Lys Met Asp Arg Ile Ser Ser Ser Ser
1               5                   10

<210> SEQ ID NO 39
<211> LENGTH: 10
<212> TYPE: PRT
<213> ORGANISM: Artificial sequence
<220> FEATURE:
<223> OTHER INFORMATION: proBNP derived sequence

<400> SEQUENCE: 39

Lys Met Asp Arg Ile Ser Ser Ser Ser Gly
1               5                   10

<210> SEQ ID NO 40
<211> LENGTH: 10
<212> TYPE: PRT
```

```
<213> ORGANISM: Artificial sequence
<220> FEATURE:
<223> OTHER INFORMATION: proBNP derived sequence

<400> SEQUENCE: 40

Met Asp Arg Ile Ser Ser Ser Ser Gly Leu
1               5                   10

<210> SEQ ID NO 41
<211> LENGTH: 10
<212> TYPE: PRT
<213> ORGANISM: Artificial sequence
<220> FEATURE:
<223> OTHER INFORMATION: proBNP derived sequence

<400> SEQUENCE: 41

Asp Arg Ile Ser Ser Ser Ser Gly Leu Gly
1               5                   10

<210> SEQ ID NO 42
<211> LENGTH: 10
<212> TYPE: PRT
<213> ORGANISM: Artificial sequence
<220> FEATURE:
<223> OTHER INFORMATION: proBNP derived sequence

<400> SEQUENCE: 42

Arg Ile Ser Ser Ser Ser Gly Leu Gly Cys
1               5                   10

<210> SEQ ID NO 43
<211> LENGTH: 10
<212> TYPE: PRT
<213> ORGANISM: Artificial sequence
<220> FEATURE:
<223> OTHER INFORMATION: proBNP derived sequence

<400> SEQUENCE: 43

Ile Ser Ser Ser Ser Gly Leu Gly Cys Lys
1               5                   10

<210> SEQ ID NO 44
<211> LENGTH: 10
<212> TYPE: PRT
<213> ORGANISM: Artificial sequence
<220> FEATURE:
<223> OTHER INFORMATION: proBNP derived sequence

<400> SEQUENCE: 44

Ser Ser Ser Ser Gly Leu Gly Cys Lys Val
1               5                   10

<210> SEQ ID NO 45
<211> LENGTH: 10
<212> TYPE: PRT
<213> ORGANISM: Artificial sequence
<220> FEATURE:
<223> OTHER INFORMATION: proBNP derived sequence

<400> SEQUENCE: 45

Ser Ser Ser Gly Leu Gly Cys Lys Val Leu
1               5                   10

<210> SEQ ID NO 46
<211> LENGTH: 10
<212> TYPE: PRT
<213> ORGANISM: Artificial sequence
```

-continued

<220> FEATURE:
<223> OTHER INFORMATION: proBNP derived sequence

<400> SEQUENCE: 46

Ser Ser Gly Leu Gly Cys Lys Val Leu Arg
1               5                   10

<210> SEQ ID NO 47
<211> LENGTH: 10
<212> TYPE: PRT
<213> ORGANISM: Artificial sequence
<220> FEATURE:
<223> OTHER INFORMATION: proBNP derived sequence

<400> SEQUENCE: 47

Ser Gly Leu Gly Cys Lys Val Leu Arg Arg
1               5                   10

<210> SEQ ID NO 48
<211> LENGTH: 10
<212> TYPE: PRT
<213> ORGANISM: Artificial sequence
<220> FEATURE:
<223> OTHER INFORMATION: proBNP derived sequence

<400> SEQUENCE: 48

Gly Leu Gly Cys Lys Val Leu Arg Arg His
1               5                   10

<210> SEQ ID NO 49
<211> LENGTH: 7
<212> TYPE: PRT
<213> ORGANISM: Artificial sequence
<220> FEATURE:
<223> OTHER INFORMATION: proBNP derived sequence

<400> SEQUENCE: 49

Gly Cys Phe Gly Arg Lys Met
1               5

<210> SEQ ID NO 50
<211> LENGTH: 7
<212> TYPE: PRT
<213> ORGANISM: Artificial sequence
<220> FEATURE:
<223> OTHER INFORMATION: proBNP derived sequence

<400> SEQUENCE: 50

Cys Phe Gly Arg Lys Met Asp
1               5

<210> SEQ ID NO 51
<211> LENGTH: 7
<212> TYPE: PRT
<213> ORGANISM: Artificial sequence
<220> FEATURE:
<223> OTHER INFORMATION: proBNP derived sequence

<400> SEQUENCE: 51

Phe Gly Arg Lys Met Asp Arg
1               5

<210> SEQ ID NO 52
<211> LENGTH: 7
<212> TYPE: PRT
<213> ORGANISM: Artificial sequence
<220> FEATURE:

```
<223> OTHER INFORMATION: proBNP derived sequence

<400> SEQUENCE: 52

Gly Arg Lys Met Asp Arg Ile
1               5

<210> SEQ ID NO 53
<211> LENGTH: 7
<212> TYPE: PRT
<213> ORGANISM: Artificial sequence
<220> FEATURE:
<223> OTHER INFORMATION: proBNP derived sequence

<400> SEQUENCE: 53

Arg Lys Met Asp Arg Ile Ser
1               5

<210> SEQ ID NO 54
<211> LENGTH: 5
<212> TYPE: PRT
<213> ORGANISM: Artificial sequence
<220> FEATURE:
<223> OTHER INFORMATION: proBNP derived sequence

<400> SEQUENCE: 54

Ser Pro Lys Met Val
1               5

<210> SEQ ID NO 55
<211> LENGTH: 6
<212> TYPE: PRT
<213> ORGANISM: Artificial sequence
<220> FEATURE:
<223> OTHER INFORMATION: proBNP derived sequence

<400> SEQUENCE: 55

Arg Ala Pro Arg Ser Pro
1               5

<210> SEQ ID NO 56
<211> LENGTH: 9
<212> TYPE: PRT
<213> ORGANISM: Artificial sequence
<220> FEATURE:
<223> OTHER INFORMATION: proBNP derived sequence

<400> SEQUENCE: 56

Pro Arg Ser Pro Lys Met Val Gln Gly
1               5

<210> SEQ ID NO 57
<211> LENGTH: 8
<212> TYPE: PRT
<213> ORGANISM: Artificial sequence
<220> FEATURE:
<223> OTHER INFORMATION: proBNP derived sequence

<400> SEQUENCE: 57

Ala Pro Arg Ser Pro Lys Met Val
1               5

<210> SEQ ID NO 58
<211> LENGTH: 8
<212> TYPE: PRT
<213> ORGANISM: Artificial sequence
<220> FEATURE:
<223> OTHER INFORMATION: proBNP derived sequence
```

```
<400> SEQUENCE: 58

Ser Gly Leu Gly Cys Lys Val Leu
1               5

<210> SEQ ID NO 59
<211> LENGTH: 9
<212> TYPE: PRT
<213> ORGANISM: Artificial sequence
<220> FEATURE:
<223> OTHER INFORMATION: proBNP derived sequence

<400> SEQUENCE: 59

Ser Pro Lys Met Val Gln Gly Ser Gly
1               5

<210> SEQ ID NO 60
<211> LENGTH: 13
<212> TYPE: PRT
<213> ORGANISM: Artificial sequence
<220> FEATURE:
<223> OTHER INFORMATION: proBNP derived sequence

<400> SEQUENCE: 60

Tyr Thr Leu Arg Ala Pro Arg Ser Pro Lys Met Val Gly
1               5                   10

<210> SEQ ID NO 61
<211> LENGTH: 12
<212> TYPE: PRT
<213> ORGANISM: Artificial sequence
<220> FEATURE:
<223> OTHER INFORMATION: proBNP derived sequence

<400> SEQUENCE: 61

Phe Gly Arg Lys Met Asp Arg Ile Ser Ser Ser Ser
1               5                   10

<210> SEQ ID NO 62
<211> LENGTH: 7
<212> TYPE: PRT
<213> ORGANISM: Artificial sequence
<220> FEATURE:
<223> OTHER INFORMATION: proBNP derived sequence

<400> SEQUENCE: 62

Ala Gly Arg Lys Met Asp Arg
1               5

<210> SEQ ID NO 63
<211> LENGTH: 11
<212> TYPE: PRT
<213> ORGANISM: Artificial sequence
<220> FEATURE:
<223> OTHER INFORMATION: proBNP derived sequence

<400> SEQUENCE: 63

Gly Cys Phe Gly Arg Lys Met Asp Arg Ile Ser
1               5                   10

<210> SEQ ID NO 64
<211> LENGTH: 11
<212> TYPE: PRT
<213> ORGANISM: Artificial sequence
<220> FEATURE:
<223> OTHER INFORMATION: proBNP derived sequence
```

```
<400> SEQUENCE: 64

Ser Phe Gly Arg Lys Met Asp Arg Ile Ser Ser
1               5                   10

<210> SEQ ID NO 65
<211> LENGTH: 18
<212> TYPE: PRT
<213> ORGANISM: Artificial sequence
<220> FEATURE:
<223> OTHER INFORMATION: proBNP derived sequence

<400> SEQUENCE: 65

Cys Phe Gly Arg Lys Met Asp Arg Ile Ser Ser Ser Gly Leu Gly
1               5                   10                  15

Cys Lys

<210> SEQ ID NO 66
<211> LENGTH: 12
<212> TYPE: PRT
<213> ORGANISM: Artificial sequence
<220> FEATURE:
<223> OTHER INFORMATION: proBNP derived sequence

<400> SEQUENCE: 66

Tyr Thr Leu Arg Ala Pro Arg Ser Pro Lys Met Val
1               5                   10

<210> SEQ ID NO 67
<211> LENGTH: 14
<212> TYPE: PRT
<213> ORGANISM: Artificial sequence
<220> FEATURE:
<223> OTHER INFORMATION: proBNP derived sequence

<400> SEQUENCE: 67

Tyr Thr Leu Arg Ala Pro Arg Ser Pro Lys Met Val Gln Gly
1               5                   10

<210> SEQ ID NO 68
<211> LENGTH: 11
<212> TYPE: PRT
<213> ORGANISM: Artificial sequence
<220> FEATURE:
<223> OTHER INFORMATION: proBNP derived sequence

<400> SEQUENCE: 68

Ser Gly Leu Gly Cys Lys Val Leu Arg Arg His
1               5                   10

<210> SEQ ID NO 69
<211> LENGTH: 9
<212> TYPE: PRT
<213> ORGANISM: Artificial sequence
<220> FEATURE:
<223> OTHER INFORMATION: proBNP derived sequence

<400> SEQUENCE: 69

Ser Gly Leu Gly Cys Lys Val Leu Arg
1               5
```